United States Patent
Yi et al.

(10) Patent No.: US 10,485,786 B2
(45) Date of Patent: Nov. 26, 2019

(54) PHARMACEUTICAL COMPOSITION FOR PREVENTING OR TREATING MACULAR DEGENERATION

(71) Applicants: KOREA RESEARCH INSTITUTE OF CHEMICAL TECHNOLOGY, Daejeon (KR); CATHOLIC UNIVERSITY INDUSTRY ACADEMIC COOPERATION FOUNDATION, Seoul (KR)

(72) Inventors: Kyu-Yang Yi, Daejeon (KR); Sung-Eun Yoo, Gongju-si (KR); Nack-Jeong Kim, Daejeon (KR); Jee-Hee Suh, Daejeon (KR); Choun-Ki Joo, Seoul (KR); Jun-Sub Choi, Yongin-si (KR); Jae-Sik Yang, Yongin-si (KR); Geun-Hyeog Lee, Yongin-si (KR); Yun-Seok Cho, Suwon-si (KR); Jin-Ha Park, Anyang-si (KR); Hye-Sung Lee, Seoul (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 15/941,856

(22) Filed: Mar. 30, 2018

(65) Prior Publication Data

US 2018/0221343 A1 Aug. 9, 2018

Related U.S. Application Data

(63) Continuation-in-part of application No. 14/008,112, filed as application No. PCT/KR2012/002310 on Mar. 29, 2011, now abandoned.

(30) Foreign Application Priority Data

Mar. 30, 2011 (KR) .......................... 10-2011-002846

(51) Int. Cl.
*A61K 31/4178* (2006.01)
*A61K 9/08* (2006.01)
*A61K 9/00* (2006.01)
*A61P 27/02* (2006.01)

(52) U.S. Cl.
CPC ........ *A61K 31/4178* (2013.01); *A61K 9/0048* (2013.01); *A61K 9/08* (2013.01); *A61P 27/02* (2018.01)

(58) Field of Classification Search
CPC .. A61K 31/417; A61K 31/351; A61K 9/0048; A61K 9/008; A61K 9/107
See application file for complete search history.

(56) References Cited

U.S. PATENT DOCUMENTS

| 2010/0120873 A1* | 5/2010 | Hirai | .................... A61K 9/0019 514/359 |
| 2014/0018402 A1* | 1/2014 | Yi | ...................... A61K 31/4178 514/397 |

FOREIGN PATENT DOCUMENTS

WO  WO-2007064752 A2 * 6/2007 ........... A61K 31/506

OTHER PUBLICATIONS

Choi et al (Affidavit of U.S. Appl. No. 14/008,112, made available to the public on Mar. 9, 2017) (Year: 2017).*
Park (International Journal of Oncology Vo. 32 pp. 1311-1314 published 2008) (Year: 2008).*
Palanki, M. et al., (Journal of Medicinal Chemistry vol. 51 pp. 1546-1559). Published 2008. (Year: 2008).*
Stern et al., Cell Stem Cell vol. 22 pp. P834-P849. Published 2018 (Year: 2018).*
Palanki et al., (J. Med. Chem. Vo. 51 pp. 1546-1559 published 2008). (Year: 2008).*

* cited by examiner

*Primary Examiner* — Timothy P Thomas
*Assistant Examiner* — George W Kosturko
(74) *Attorney, Agent, or Firm* — Vorys, Sater, Seymour and Pease LLP; Mih Suhn Koh

(57) ABSTRACT

The present invention provides a pharmaceutical composition for preventing or treating macular degeneration, which comprises benzopyran derivatives substituted with secondary amines including imidazole or pharmaceutically acceptable salts thereof as an active ingredient. The pharmaceutical composition of the present invention may be used in the form of eye drops.

4 Claims, 9 Drawing Sheets

Control (BSS)  Eyedrop (0.9mg/ml)  Eyedrop (0.6mg/ml)  Suspension (0.6mg/ml)

| | Vehicle (control) | KR-31831 | TG 100801 | ATG-003 | Pazopanib |
|---|---|---|---|---|---|
| Mean | 88.454084 | 87.346538 | 72.618853 | 74.049058 | 80.2671 |
| SD | 3.738415 | 3.344245 | 4.286309 | 4.1213991 | 2.749849 |

In after 18 hours, Significance (One way anova analysis)
P = 0.00000191

In after 18 hours, Significance (One way anova analysis)
P = 0.00000191

PHARMACEUTICAL COMPOSITION FOR PREVENTING OR TREATING MACULAR DEGENERATION

CROSS-REFERENCE TO RELATED APPLICATIONS

This application is a Continuation-in-Part application of U.S. patent application Ser. No. 14/008,112 filed on Sep. 27, 2013, which is a 371 of international application PCT/KR2012/002310 filed on Mar. 29, 2011, which claims priority from and the benefit under 35 USC 119(a) of Korean Patent Application number 10-2011-002846 filed on Mar. 30, 2011, each of which is hereby incorporated by reference.

TECHNICAL FIELD

The present invention relates to a pharmaceutical composition for preventing or treating macular degeneration, which comprises benzopyran derivatives substituted with secondary amines including imidazole; or pharmaceutically acceptable salts thereof as an active ingredient.

BACKGROUND ART

The nerve tissue located at the center of the retina of the eye is called as a macula. The macula includes most of phtoreceptor cells responding to light stimuli; and the appearances of objects are focused at the center of the macula. Therefore, the macular plays an essential role in maintaining eyesight. Age-related macular degeneration (AMD) is a chronic disease characterized by the degenerations in the retinal pigment epithelium and Bruch's membrane in the macular as well as the choroidal capillary. Anatomically, the sensory retina is located in front of the retinal pigment epithelium. The nutrition, support, recycling, and treatment of wastes of the sensory retina depend on the retinal pigment epithelium. Bruch's membrane having a five-layered structure is sandwiched between the choroid and the retinal pigment epithelium. The innermost layer is a basal membrane of the retinal pigment epithelium; and the outermost layer is a basal membrane of the choroidal capillary. That is, the macular degeneration is a degenerative disease occurred in the complex of the retinal pigment epithelium, Bruch's membrane, and the choroidal capillary.

This disease, which occurs primarily in the ages over 50 years old, is the main cause of blindness in the population of more than 60 years old in the Western countries; and the trend thereof is also increasing in Korea. Although the cause of age-related macular degeneration is not still elucidated, the risk factors include age (especially, sharp increase is shown after the age of 75 years old), smoking (most notable environmental risk factor), high blood pressure, obesity, genetic cause, excessive UV exposure, low blood concentration of antioxidant, and the like.

In the macular degeneration, there are two types, i.e., dry (non-exudative) macular degeneration and wet (exudative) macular degeneration. The dry macular degeneration (dry AMD, non-exudative AMD, or non-neovascular AMD) is associated with the waste formation of yellow deposits, known as drusen, under the retina. The large formation of drusen causes disturbing the blood flow to the retina, especially to the macular, which leads to obscure vision, thereby bring about visual impairment. Although the dry macular degeneration does not cause a sudden loss of vision, it may be developed to a wet macular degeneration. Under the retina, there are the choroid containing a set of vessels buried within the fibrous tissue and the pigment epithelium covering the choroid layer. The wet macular degeneration (wet AMD, exudative AMD, or neovascular AMD) is associated with the angiogenesis from the choroid area under the retina. The burst of these weak neovessels causes hemorrhage and exudation, which leads to degeneration in the macula area of the retina, thereby bring about visual impairment. Because the wet macular degeneration is developed very rapidly, it is known that vision can be deteriorated in several weeks; or that loss of vision can be caused between 2 month and 3 years.

As a therapy for macular degeneration, a photodynamic therapy (PDT) and an injection therapy of antibody against angiogenic growth factor are currently being used. The photodynamic therapy is a method which comprises injecting a photosensitizer, Visudyne, through the blood vessels, followed by irradiation of the eye with a specific laser reactive only to the photosensitizer at the time when the photosensitizer arrives at neovessels of the retina, so as to selectively destroy the neovessels. However, the photodynamic therapy causes many recurrent cases after the treatment, which requires repetitive treatments. And also, there is a drawback that the repetitive treatments causes damage of the retina itself. The antibody injection therapy is a method injecting directly into the retina an anti-VEGF antibody which inhibits the formation and proliferation of neovessels through selectively binding to the vascular endothelial growth factor (VEGF) critical to the formation and progression of neovessels. As a protein drug used in the antibody injection therapy, there are Lucentis and Avastin. Lucentis has been approved by the FDA as a therapeutic agent of wet macular degeneration. Although Avastin is approved to treat cancer, it is being clinically used to treat wet AMD.

The antibody injection therapy has some drawbacks: for example, it requires high therapeutic cost, local administration (especially direct administration into the eye), and repeated injections. Therefore, in terms of patients' drug compliance, therapeutic cost, etc., there is a need for developing an (non-injectable) eye drop formulation based on a low-molecular weight synthetic compound.

DETAILED DESCRIPTION OF THE INVENTION

Technical Problem

The present inventors performed various researches for developing effective compounds for preventing and treating macular degeneration. As a result, the present inventors found that certain benzopyran derivatives having therapeutic effects for cancer, rheumatoid arthritis, etc. previously reported by the present inventors can be prepared as an eye drop formulation based on a low-molecular weight material; and usefully applied to the prevention and treatment of macular degeneration, without injecting directly into the affected site as in the antibody injection therapy.

Therefore, it is an object of the present invention to provide a pharmaceutical composition for preventing or treating macular degeneration, which comprises a certain benzopyran derivative as an active ingredient.

Technical Solution

According to an aspect of the present invention, there is provided a pharmaceutical composition for preventing or treating macular degeneration, which comprises a compound of Formula 1 or its pharmaceutically acceptable salt as an active ingredient:

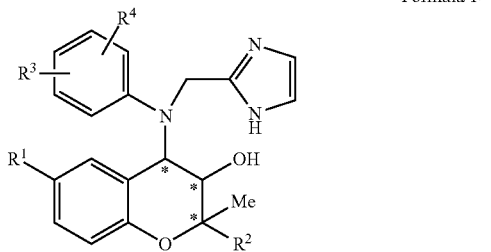

<Formula 1> wherein,
$R^1$ represents H, CN, $NO_2$ or $NH_2$,
$R^2$ represents

$R^3$ and $R^4$ are independent each other and represent H, Cl, Br, F, $C_1$~$C_3$ straight or branched alkyl, $OR^b$, $CF_3$, $OCF_3$, $NO_2$ or $CO_2R^b$,
$R^a$ represents $C_1$~$C_4$ straight or branched alkyl,
$R^b$ represents H or $C_1$~$C_3$ alkyl, and
* represents the chiral center.

In an embodiment of the present invention, there is provided a pharmaceutical composition for preventing or treating macular degeneration, which comprises (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its pharmaceutically acceptable salt as an active ingredient.

In another embodiment of the present invention, there is provided an eye drop formulation for preventing or treating macular degeneration, which comprises (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its pharmaceutically acceptable salt as an active ingredient. The eye drop formulation may have a solution form or a suspension form.

Advantageous Effects

It is newly found by the present invention that the compound of Formula 1 or its pharmaceutically acceptable salt may be usefully applied to the prevention and treatment of macular degeneration, the degenerative disease of retinal choroidal capillary. Especially, it is found by the present invention that, when (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its pharmaceutically acceptable salt is administered to the cornea in the form of eye drops, it is delivered to the retina without inhibiting normal regeneration of corneal epithelial cells. Therefore, the compound of Formula 1, including (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran, or its pharmaceutically acceptable salt can be usefully applied for preventing or treating macular degeneration in an eye drop formulation.

BEST MODE FOR CARRYING OUT THE INVENTION

Figure 1:
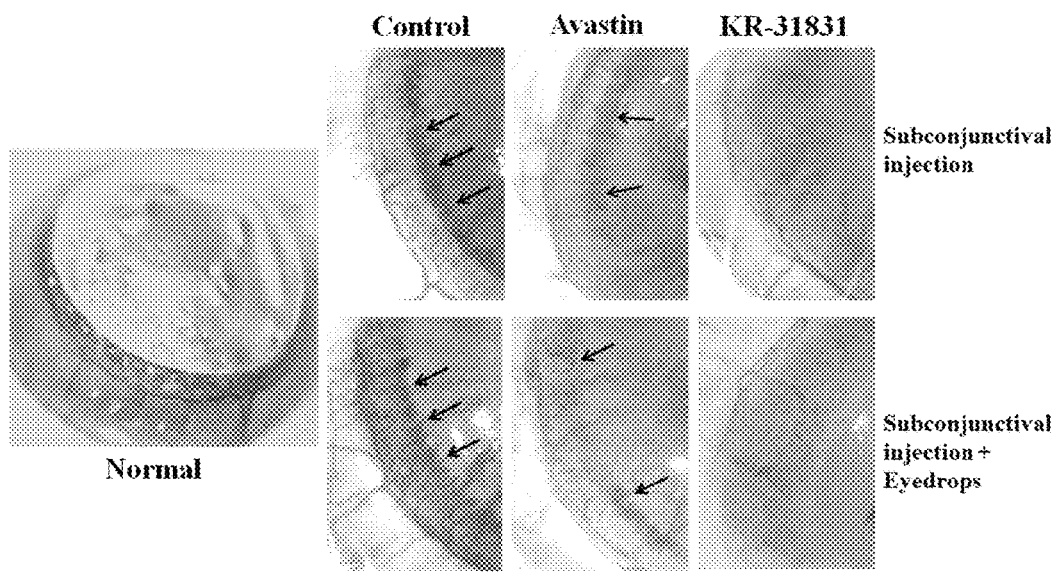
FIG. 1 is the results (photographs) obtained by evaluating inhibitory effects against corneal angiogenesis in animal models with corneal damage.

There is provided a pharmaceutical composition for preventing or treating macular degeneration, which comprises a compound of Formula 1 or its pharmaceutically acceptable salt as an active ingredient:

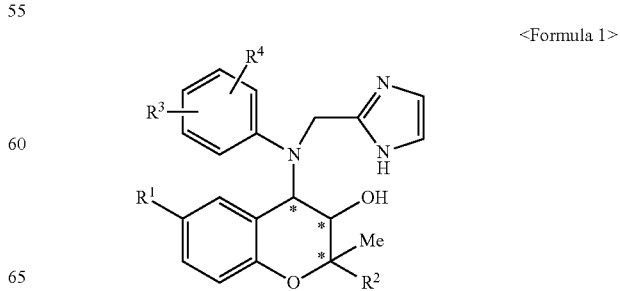

<Formula 1> wherein,
R¹ represents H, CN, NO₂ or NH₂,
R² represents $$CH\begin{matrix}OR^a,\\OR^a\end{matrix}$$

R³ and R⁴ are independent each other and represent H, Cl, Br, F, $C_1$~$C_3$ straight or branched alkyl, $OR^b$, $CF_3$, $OCF_3$, $NO_2$ or $CO_2R^b$,
$R^a$ represents $C_1$~$C_4$ straight or branched alkyl,
$R^b$ represents H or $C_1$~$C_3$ alkyl, and
* represents the chiral center.

In the pharmaceutical composition according to the present invention, the compound of Formula 1 may be selected from the group consisting of:

(2S,3S,4R)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2S,3R,4S)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2R,3S,4R)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(4-trifluoromethylphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(4-methoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(4-bromophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(2,4-dimethylphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(2-isopropylphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(4-bromophenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(4-methoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(4-fluorophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(2-methoxyphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(2-isopropylphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(2-methoxyphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(3-chlorophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-nitro-4-[N-(3-chlorophenyl)-N-(1H-imidazol-2-ylmethyl)amino]-3-hydroxy-2-methyl-2-dimethoxymethyl-3,4-dihydro-2H-1-benzopyran;
(2R,3R,4S)-6-nitro-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-cyano-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(4-trifluoromethylphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-amino-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-amino-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-amino-4-[N-(4-methoxyphenyl)-N-(1H-imidazol-2-ylmethyl)amino]-3-hydroxy-2-methyl-2-dimethoxymethyl-3,4-dihydro-2H-1-benzopyran;
(2R,3R,4S)-6-amino-4-[N-(4-bromophenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(2-methoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(4-methoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(2,4-dimethylphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(2-isopropylphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran;
(2S,3S,4R)-6-amino-4-[N-(4-bromophenyl)-N-(1H-imidazol-2-ylmethyl)amino]-3-hydroxy-2-methyl-2-dimethoxymethyl-3,4-dihydro-2H-1-benzopyran; and
(2S,3S,4R)-6-amino-4-[N-(4-fluorophenyl)-N-(1H-imidazol-2-ylmethyl)amino]-3-hydroxy-2-methyl-2-dimethoxymethyl-3,4-dihydro-2H-1-benzopyran.

Among the compounds of Formula 1, especially preferable compound is (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its pharmaceutically acceptable salt. Therefore, in an embodiment of the present invention, there is provided a pharmaceutical composition for preventing or treating macular degeneration, which comprises (2R,3R,4S)-6-amino-4-[N-(4-chlorophenyl)-N-(1H-imidazol-2-ylmethyl)amino]-3-hydroxy-2-methyl-2-dim ethoxymethyl-3,4-dihydro-2H-1-benzopyran or its pharmaceutically acceptable salt as an active ingredient.

The compound of Formula 1 may be used as a pharmaceutically acceptable salt, including e.g., an acid addition salt derived from pharmaceutically acceptable free acids, an alkali metal salt (sodium salt, potassium salt, etc.), and an alkali earth metal salt (calcium salt, magnesium salt, etc.). The free acid includes an inorganic acid and an organic acid. The inorganic acid includes hydrochloric acid, hydrobromic acid, nitric acid, sulfuric acid, perchloric acid, phosphoric acid, etc. The organic acid includes citric acid, acetic acid, lactic acid, maleic acid, fumaric acid, gluconic acid, methanesulfonic acid, glycolic acid, succinic acid, tartaric acid, galacturonic acid, embonic acid, glutamic acid, aspartic acid, oxalic acid, (D) or (L) malic acid, maleic acid, methanesulfonic acid, ethanesulfonic acid, 4-toluenesulfonic acid, salicylic acid, citric acid, benzoic acid, malonic acid, etc. Examples of the pharmaceutically acceptable salt of the compound of Formula 1 include acetate, aspartate, benzoate, besylate, bicarbonate/carbonate, bisulfate/sulfate, borate, camsylate, citrate, edicylate, ecylate, formate, fumarate, gluceptate, gluconate, glucuronate, hexafluorophosphate, hibenzate, hydrochloride/chloride, hydrobromide/bromide, hydroiodide/iodide, isethionate, latate, malate, maleate, malonate, mesylate, methylsulfate, naphthylate, 2-napsylate, nicotinate, nitrate, orotate, oxalate, palmitate, famoate, phosphate/hydrogen phosphate/dihydrogen phosphate, saccharate, stearate, succinate, tartrate, tosylate, trifluoroacetate, aluminium salt, arginine salt, benzathine salt, calcium salt, choline salt, diethylamine salt, diolamine salt, glycine salt, lysine salt, magnesium salt, meglumine salt, olamine salt, potassium salt, sodium salt, tromethamine salt, zinc salt, etc. Among them, hydrochloride and/or trifluoroacetate are preferable.

The pharmaceutically acceptable salt of the compound of Formula 1 may be prepared according to conventional methods. For example, the acid addition salt may be prepared by dissolving the compound of Formula 1 in a water-miscible organic solvent, such as acetone, methanol, ethanol, or acetonitrile; and then adding an organic acid in excess or an aqueous solution of an inorganic acid, so as to precipitate or crystallize the resulting salt. Subsequently, the acid addition salt may be isolated by evaporating the solvent or the excessive acid and then drying the resulting residue; or by suction-filtering the precipitated salt.

And also, the compound of Formula 1 or its pharmaceutically acceptable salt includes its isomers, hydrates, and solvates.

The compound of Formula 1 or its pharmaceutically acceptable salt shows an inhibitory activity against corneal angiogenesis and inhibitory activity against expression of corneal angiogenesis marker, FLK-1 (see FIGS. 1 to 4). The normal healing ability (regeneration ability) of corneal epithelial cells is not inhibited by the pharmaceutical composition of the present invention (see FIGS. 5 and 6). And also, the compound of Formula 1 or its pharmaceutically acceptable salt shows excellent activity for preventing or treating macular degeneration, a disease induced by degeneration of the retinal choroidal capillary (see FIGS. 7 to 10). Especially, it is found by the present invention that the compound of Formula 1 or its pharmaceutically acceptable salt may be prepared into a topically administrable external eye drop formulation form, which shows excellent activity for preventing or treating macular degeneration without injecting into the affected site (see FIGS. 11 and 12). In addition, it is found by the present invention that, when the eye drop formulation is administered to the cornea, the active ingredient is effectively delivered to the retina, while only a negligible amount is absorbed into the blood (see Table 1).

Therefore, the present invention includes, within its scope, an eye drop formulation for preventing or treating macular degeneration, which comprises a compound of Formula 1 or its pharmaceutically acceptable salt as an active ingredient. In an embodiment of the present invention, there is provided an eye drop formulation for preventing or treating macular degeneration, which comprises (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its pharmaceutically acceptable salt as an active ingredient. The eye drop formulation may have a solution form or a suspension form. In an embodiment, the eye drop formulation may comprise the active ingredient (e.g., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt) in a therapeutically effective concentration ranging, for example from 0.1 mg/mL to 20 mg/mL, preferably from 1 mg/mL to 15 mg/mL, more preferably from 3 mg/mL to 10 mg/mL. In another embodiment, the eye drop formulation may comprise (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt in a concentration of about 3 mg/mL, about 6 mg/mL, or about 10 mg/mL. Said eye drop formulation may be applied to the cornea of an eye in a single administration or in multiple administrations, for example from 1 to 6 times per day, preferably from 2 to 4 times per day.

For example, an eye drop formulation in a solution form may comprises a solubilizer such as polyethylene glycol 400, glycerin, etc.; a stabilizer such as EDTA etc.; a buffering agent such as boric acid etc.; a pH controlling agent such as hydrochloric acid, sodium hydroxide, etc., in addition to the compound of Formula 1 or its pharmaceutically acceptable salt (for example, (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its salt). And also, an eye drop formulation in a suspension form may comprises a viscosity controlling agent such as cross-linked polyvinylpyrrolidone (for example, povidone K-25) etc.; an isotonic agent such as sodium chloride, etc.; a stabilizer such as EDTA etc.; a buffering agent such as boric acid, Borax, etc.; a pH controlling agent such as hydrochloric acid, sodium hydroxide, etc., in addition to the compound of Formula 1 or its pharmaceutically acceptable salt (for example, (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or its salt). If necessary, the pharmaceutical composition in the eye drop formulation form may be sterilized according to conventional methods; or further comprise a supplement agent such as a preservative, a hydrating agent, an emulsifier, a solubilizing agent, a salt for controlling osmotic pressure, and/or a buffering agent.

In the pharmaceutical composition of the present invention, the compound of Formula 1 or its pharmaceutically acceptable salt may be administered in an amount of typically about 0.01 to about 100 mg/day, preferably 0.03 to 80 mg/day based on adults having 70 Kg of body weight, although the amount may be changed according to the patient's age, body weight, sex, dosage form, health condition, severity of disease, etc. The administration may be carried out in an appropriate interval, e.g., in a single dose or in divided doses per day, according to the doctor's or pharmacist's instruction.

The present invention includes, within its scope, a use of a compound of Formula 1 or its pharmaceutically acceptable salt for the manufacture of a medicament for preventing or treating macular degeneration:

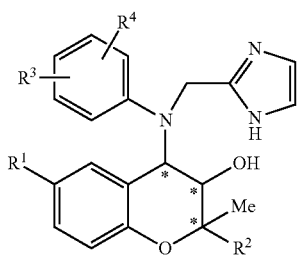

<Formula 1> wherein, $R^1$, $R^2$, $R^3$ and $R^4$ are the same as defined in the above; and * represents the chiral center.

In the use of the present invention, the compound of Formula 1 may be preferably (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran. The medicament may have a solution form or a suspension form. In the use of the present invention, the compound of Formula 1 or its pharmaceutically acceptable salt may be administered in an amount of typically about 0.01 to about 100 mg/day, preferably 0.03 to 80 mg/day based on adults having 70 Kg of body weight, although the amount may be changed according to the patient's age, body weight, sex, dosage form, health condition, severity of disease, etc. The administration can be carried out in an appropriate interval, e.g., in a single dose or in divided doses per day, according to the doctor's or pharmacist's instruction.

The present invention also includes, within its scope, a method for preventing or treating macular degeneration in a patient, which comprises administering a therapeutically effective amount of the compound of Formula 1 or its pharmaceutically acceptable salt to the patient in need thereof:

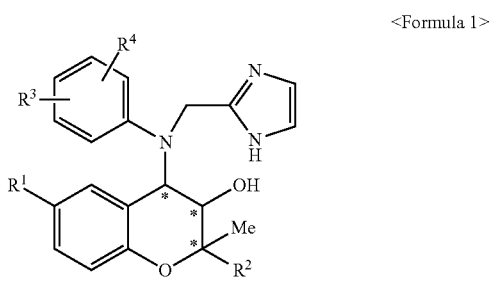

<Formula 1> wherein, $R^1$, $R^2$, $R^3$ and $R^4$ are the same as defined in the above; and * represents the chiral center.

In the method for preventing or treating macular degeneration of the present invention, the compound of Formula 1 may be preferably (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran. The compound may be administered in an eye drop formulation having a solution form or a suspension form. In the method for preventing or treating macular degeneration of the present invention, the compound of Formula 1 or its pharmaceutically acceptable salt may be administered in an amount of typically about 0.01 to about 100 mg/day, preferably 0.03 to 80 mg/day based on adults with 70 Kg of body weight, although the amount may be changed according to the patient's age, body weight, sex, dosage form, health condition, severity of disease, etc. The administration can be carried out in an appropriate interval, e.g., in a single dose or in divided doses per day, according to the doctor's or pharmacist's instruction.

The present invention will be described in further detail with reference to the following preparation examples and examples. These e preparation examples and examples are for illustrative purposes only and are not intended to limit the scope of the present invention.

PREPARATION EXAMPLE 1

Preparation of (2S,3S,4R)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran The epoxide compound, (2S,3S,4R)-6-nitro-2-methyl-2-dimethoxymethyl-3,4-epoxy-3,4-dihydro-2H-1-benzopyran (437 mg, 1.55 mmol) and (4-chlorophenyl)(1H-imidazol-2-ylmethyl)amine (323 mg, 1.55 mmol) were dissolved in acetonitrile (2 mL). To the resulting solution was added anhydrous cobalt chloride ($CoCl_2$) (202 mg, 1.55 mmol). The reaction mixture was stirred at 60° C. for 10 hours; and then a saturated aqueous solution of $NaHCO_3$ (5 mL) was added to the mixture, which was extracted with ethyl acetate (30 mL). The organic layer was washed with brine, dried over anhydrous $Na_2SO_4$, and then concentrated under reduced pressure. The resulting residue was purified with silica gel column chromatography (hexane:ethyl acetate=2:1) to give the title compound (304 mg, 40%).

$^1$H NMR (200 MHz, $CDCl_3$) δ 1.49(s, 3H), 3.60(s, 3H), 3.63(s, 3H), 4.32(m, 1H), 4.57(s, 1H), 5.14(br s, 1H), 6.75(br s, 2H), 6.97(m, 4H), 7.27(m, 2H), 7.93(s, 1H), 8.08(d, 1H).

PREPARATION EXAMPLE 2

Preparation of (2S,3R,4S)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran The title compound (76 mg, 34%) was prepared in accordance with the same procedures as in Preparation Example 1, using the epoxide compound, (2S,3R,4R)-6-nitro-2-methyl-2-dimethoxymethyl-3,4-epoxy-3,4-dihydro-2H-1-benzopyran (129 mg, 0.46 mmol) and (4-chlorophenyl)(1H-imidazol-2-ylmethyl)amine (95 mg, 0.46 mmol).

$^1$H NMR (200 MHz, $CDCl_3$) δ 1.66(s, 3H), 3.60(s, 3H), 3.69(s, 3H), 3.87(br s, 1H), 4.13(m, 1H), 4.29(d, 1H), 4.43(d, 1H), 4.64(s, 1H), 5.64(d, 1H), 6.83(d, 2H), 6.95(m, 4H), 7.15(d, 2H), 7.86(s, 1H), 8.06(m, 2H), 8.41(s, 1H).

PREPARATION EXAMPLE 3

Preparation of (2R,3R,4S)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran The title compound (2.13 g, 64%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (1.038 g, 3.7 mmol) and (4-chlorophenyl)(1H-imidazol-2-ylmethyl)amine (766 mg, 3.7 mmol).

$^1$H NMR (200 MHz, CDCl$_3$) δ 1.49(s, 3H), 3.60(s, 3H), 4.32(m, 1H), 4.57(s, 1H), 5.14(br s, 1H), 6.75(br s, 2H), 6.97(m, 4H), 7.27(m, 2H), 7.93(s, 1H), 8.08(d, 1H).

PREPARATION EXAMPLE 4

Preparation of (2R,3S,4R)-6-nitro-4-[N-(4-chlorophenyl)-N-(1H-imidazol-2-ylmethyl)amino]-3-hydroxy-2-methyl-2-dimethoxymethyl-3,4-dihydro-2H-1-benzopyran The title compound (269 mg, 63%) was prepared in accordance with the same procedures as in Preparation Example 1, using the epoxide compound, (2R,3S,4S)-6-nitro-2-methyl-2-dimethoxymethyl-3,4-epoxy-3,4-dihydro-2H-1-benzopyran (250 mg, 0.88 mmol) and (4-chlorophenyl)(1H-imidazol-2-ylmethyl)amine (183 mg, 0.88 mmol).

$^1$H NMR (200 MHz, CDCl$_3$) δ 1.66(s, 3H), 3.60(s, 3H), 3.69(s, 3H), 3.87(br s, 1H), 4.13(m, 1H), 4.29(d, 1H), 4.43(d, 1H), 4.64(s, 1H), 5.64(d, 1H), 6.83(d, 2H), 6.95(m, 4H), 7.15(d, 2H), 7.86(s, 1H), 8.06(m, 2H), 8.41(s, 1H).

PREPARATION EXAMPLE 5

Preparation of (2S,3S,4R)-6-nitro-4-[N-(4-trifluoromethylphenyl)-N-(1H-imidazol-2-ylmethyl)amino]-3-hydroxy-2-methyl-2-dimethoxymethyl-3,4-dihydro-2H-1-benzopyran The title compound (146 mg, 22%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (356 mg, 1.26 mmol) and (4-trifluoromethylphenyl)(1H-imidazol-2-ylmethyl)amine (305 mg, 1.26 mmol).

$^1$H NMR (200 MHz, CDCl$_3$) δ 1.51(s, 3H), 3.60(s, 3H), 3.61(s, 3H), 4.32(m, 3H), 4.57(s, 1H), 5.14(br s, 1H), 6.85(m, 2H), 6.95(m, 4H), 7.38(d, 2H), 7.91(s, 1H), 8.05(dd, 2H), 8.42(m, 1H).

PREPARATION EXAMPLE 6

Preparation of (2S,3S,4R)-6-nitro-4-[N-(4-methoxyphenyl)-N-(1H-imidazol-2-ylmethyl)amino]-3-hydroxy-2-methyl-2-dimethoxymethyl-3,4-dihydro-2H-1-benzopyran The title compound (280 mg, 28%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (591 mg, 2.10 mmol) and (4-methoxyphenyl)(1H-imidazol-2-ylmethyl)amine (427 mg, 2.10 mmol).

$^1$H NMR (200 MHz, CDCl$_3$) δ 1.47(s, 3H), 3.59(d, 6H), 3.68(s, 3H), 4.30(m, 2H), 4.54(m, 2H), 5.02(d, 1H), 6.67-6.78(m, 4H), 6.89-7.26(m, 3H), 8.04(m, 2H).

PREPARATION EXAMPLE 7

Preparation of (2S,3S,4R)-6-nitro-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran The title compound (181 mg, 47%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (200 mg, 0.71 mmol) and (4-trifluoromethoxyphenyl)(1H-imidazol-2-ylmethyl)amine (183 mg, 0.71 mmol).

$^1$H NMR (200 MHz, CDCl$_3$) δ 1.50(s, 3H), 3.60(d, 6H), 4.2-4.50(m, 2H), 4.58-5.65(m, 2H), 5.18(s, 1H), 6.91-6.95 (m, 7H), 8.00(s, 1H), 8.05(dd, 1H).

PREPARATION EXAMPLE 8

Preparation of (2S,3S,4R)-6-nitro-4-[N-(4-bromophenyl)-N-(1H-imidazol-2-ylmethyl)amino]-3-hydroxy-2-methyl-2-dimethoxymethyl-3,4-dihydro-2H-1-benzopyran The title compound (310 mg, 41%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (400 mg, 1.42 mmol) and (4-bromophenyl)(1H-imidazol-2-ylmethyl)amine (359 mg, 1.42 mmol).

$^1$H NMR (200 MHz, CDCl$_3$) δ 1.48(s, 3H), 3.61(d, 6H), 4.10-4.19(m, 2H), 4.20-4.40(m, 2H), 5.13(s, 1H), 6.70-7.01 (m, 6H), 7.21(s, 1H), 7.94(s, 1H), 8.06(dd, 1H).

PREPARATION EXAMPLE 9

Preparation of (2S,3S,4R)-6-nitro-4-[N-(2,4-dimethylphenyl)-N-(1H-imidazol-2-ylmethyl)amino]-3-hydroxy-2-methyl-2-dimethoxymethyl-3,4-dihydro-2H-1-benzopyran The title compound (231 mg, 33%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (400 mg, 1.42 mmol) and (2,4-dimethylphenyl)(1H-imidazol-2-ylmethyl)amine (287 mg, 1.42 mmol).

$^1$H NMR (200 MHz, CDCl$_3$) δ 1.39(s, 3H), 2.19(s, 3H), 2.47(s, 3H), 3.59(d, 6H), 4.15-4.82(m, 5H), 6.80-6.89(m, 5H), 7.58(d, 1H), 7.94-7.99(dd, 1H), 8.62(m, 1H).

PREPARATION EXAMPLE 10

Preparation of (2S,3S,4R)-6-nitro-4-[N-(2-isopropylphenyl)-N-(1H-imidazol-2-ylmethyl)amino]-3-hydroxy-2-methyl-2-dimethoxymethyl-3,4-dihydro-2H-1-benzopyran The title compound (140 mg, 20%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (400 mg, 1.42 mmol) and (2-isopropylphenyl)(1H-imidazol-2-ylmethyl)amine (306 mg, 1.42 mmol).

$^1$H NMR (200 MHz, CDCl$_3$) δ 1.22-1.29(m, 10H), 3.60 (d, 6H), 4.07-4.63(m, 5H), 6.79-7.35(m, 6H), 7.78(m, 1H), 7.99(dd, 1H), 8.61(m, 1H)

PREPARATION EXAMPLE 11

Preparation of (2S,3S,4R)-6-nitro-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran The title compound (253 mg, 37%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (400 mg, 1.42 mmol) and (2,3-dimethylphenyl)(1H-imidazol-2-ylmethyl)amine (287 mg, 1.42 mmol).

$^1$H NMR (200 MHz, CDCl$_3$) δ 1.39(s, 3H), 2.17(s, 3H), 2.41(s, 3H), 3.61(d, 6H), 4.26-4.74(m, 5H), 6.76-6.95(m, 4H), 6.98(m, 1H), 7.58(d, 1H), 7.95(dd, 1H), 8.63(d, 1H).

PREPARATION EXAMPLE 12

Preparation of (2R,3R,4S)-6-nitro-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran The title compound (416 mg, 49%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (500 mg, 1.77 mmol) and (2,3-dimethylphenyl)(1H-imidazol-2-ylmethyl)amine (358 mg, 1.77 mmol).

$^1$H NMR (200 MHz, CDCl$_3$) δ 1.39(s, 3H), 2.17(s, 3H), 2.41(s, 3H), 3.61(d, 6H), 4.26-4.74(m, 5H), 6.76-6.95(m, 4H), 6.98(m, 1H), 7.58(d, 1H), 7.95(dd, 1H), 8.63(d, 1H).

PREPARATION EXAMPLE 13

Preparation of (2R,3R,4S)-6-nitro-4-[N-(4-bromophenyl)-N-(1H-imidazol-2-ylmethyl)amino]-3-hydroxy-2-methyl-2-dimethoxymethyl-3,4-dihydro-2H-1-benzopyran The title compound (570 mg, 60%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (500 mg, 1.78 mmol) and (4-bromophenyl)(1H-imidazol-2-ylmethyl)amine (450 mg, 1.78 mmol).

$^1$H NMR (200 MHz, CDCl$_3$) δ 1.48(s, 3H), 3.61(d, 6H), 4.10-4.19(m, 2H), 4.20-4.40(m, 2H), 5.13(s, 1H), 6.70-7.01 (m, 6H), 7.21(s, 1H), 7.94(s, 1H), 8.06(dd, 1H).

PREPARATION EXAMPLE 14

Preparation of (2R,3R,4S)-6-nitro-4-[N-(4-methoxyphenyl)-N-(1H-imidazol-2-ylmethyl)amino]-3-hydroxy-2-methyl-2-dimethoxymethyl-3,4-dihydro-2H-1-benzopyran The title compound (446 mg, 86%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (300 mg, 1.06 mmol) and (4-methoxyphenyl)(1H-imidazol-2-ylmethyl)amine (216 mg, 1.06 mmol).

$^1$H NMR (200 MHz, CDCl$_3$) δ 1.47(s, 3H), 3.59(d, 6H), 3.68(s, 3H), 4.30(m, 2H), 4.54(m, 2H), 5.02(d, 1H), 6.67-6.78(m, 4H), 6.89-7.26(m, 3H), 8.04(m, 2H).

PREPARATION EXAMPLE 15

Preparation of (2S,3S,4R)-6-nitro-4-[N-(4-fluorophenyl)-N-(1H-imidazol-2-ylmethyl)amino]-3-hydroxy-2-methyl-2-dimethoxymethyl-3,4-dihydro-2H-1-benzopyran The title compound (650 mg, 48%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (800 mg, 2.84 mmol) and (4-fluorophenyl)(1H-imidazol-2-ylmethyl)amine (380 mg, 1.8 mmol).

$^1$H NMR (200 MHz, CDCl$_3$) δ 1.49(s, 3H), 3.60(d, 6H), 4.30(m, 2H), 4.60(m, 2H), 5.05(m, 1H), 6.76-6.97(m, 7H), 7.95(s, 1H), 8.03(dd, 1H)

PREPARATION EXAMPLE 16

Preparation of (2S,3S,4R)-6-nitro-4-[N-(2-methoxyphenyl)-N-(1H-imidazol-2-ylmethyl)amino]-3-hydroxy-2-methyl-2-dimethoxymethyl-3,4-dihydro-2H-1-benzopyran The title compound (500 mg, 58%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (500 mg, 1.78 mmol) and (2-methoxyphenyl)(1H-imidazol-2-ylmethyl)amine (253 mg, 1.25 mmol).

$^1$H NMR (200 MHz, CDCl$_3$) δ 1.38(s, 3H), 3.60(d, 6H), 3.91(s, 3H), 3.97(m, 1H), 4.74(d, 1H), 4.60-4.84(m, 3H), 6.80-7.03(m, 6H), 7.58(m, 1H), 7.99(dd, 1H), 8.86(m, 1H)

PREPARATION EXAMPLE 17

Preparation of (2R,3R,4S)-6-nitro-4-[N-(2-isopropylphenyl)-N-(1H-imidazol-2-ylmethyl)amino]-3-hydroxy-2-methyl-2-dimethoxymethyl-3,4-dihydro-2H-1-benzopyran The title compound (72 mg, 42%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (100 mg, 0.35 mmol) and (2-isopropylphenyl)(1H-imidazol-2-ylmethyl)amine (75 mg, 0.35 mmol).

$^1$H NMR (200 MHz, CDCl$_3$) δ 1.22-1.29(m, 10H), 3.60 (d, 6H), 4.07-4.63(m, 5H), 6.79-7.35(m, 6H), 7.78(m, 1H), 7.99(dd, 1H), 8.61(m, 1H).

PREPARATION EXAMPLE 18

Preparation of (2R,3R,4S)-6-nitro-4-[N-(2-methoxyphenyl)-N-(1H-imidazol-2-ylmethyl)amino]-3-hydroxy-2-methyl-2-dimethoxymethyl-3,4-dihydro-2H-1-benzopyran The title compound (580 mg, 67%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (500 mg, 1.78 mmol) and (2-methoxyphenyl)(1H-imidazol-2-ylmethyl)amine (231 mg, 1.78 mmol).

$^1$H NMR (200 MHz, CDCl$_3$) δ 1.38(s, 3H), 3.60(d, 6H), 3.91(s, 3H), 3.97(m, 1H), 4.74(d, 1H), 4.60-4.84(m, 3H), 6.80-7.03(m, 6H), 7.58(m, 1H), 7.99(dd, 1H), 8.86(m, 1H).

PREPARATION EXAMPLE 19

Preparation of (2R,3R,4S)-6-nitro-4-[N-(3-chlorophenyl)-N-(1H-imidazol-2-ylmethyl)amino]-3-hydroxy-2-methyl-2-dimethoxymethyl-3,4-dihydro-2H-1-benzopyran The title compound (337 mg, 39%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (500 mg, 1.77 mmol) and (3-chlorophenyl)(1H-imidazol-2-ylmethyl)amine (366 mg, 1.77 mmol).

$^1$H NMR (200 MHz, CDCl$_3$) δ 1.51(s, 3H), 3.61(d, 6H), 4.20-4.57(m, 2H), 4.57-4.59(m, 2H), 5.17(s, 1H), 6.69-6.73 (m, 3H), 6.94-7.01(m, 4H), 7.89(m, 1H), 8.04(dd, 1H).

PREPARATION EXAMPLE 20

Preparation of (2S,3S,4R)-6-nitro-4-[N-(3-chlorophenyl)-N-(1H-imidazol-2-ylmethyl)amino]-3-hydroxy-2-methyl-2-dimethoxymethyl-3,4-dihydro-2H-1-benzopyran The title compound (280 mg, 35%) was prepared in accordance with the same procedures as in Preparation Example 1, using the epoxide compound, (2S,3S,4S)-6-nitro-2-methyl-2-dimethoxymethyl-3,4-epoxy-3,4-dihydro-2H-1-benzopyran (450 mg, 1.6 mmol) and (3-chlorophenyl)(1H-imidazol-2-ylmethyl)amine (232 mg, 1.1 mmol).

$^1$H NMR (200 MHz, CDCl$_3$) δ 1.51(s, 3H), 3.61(d, 6H), 4.20-4.57(m, 2H), 4.57-4.59(m, 2H), 5.17(s, 1H), 6.69-6.73 (m, 3H), 6.94-7.01(m, 4H), 7.89(m, 1H), 8.04(dd, 1H).

PREPARATION EXAMPLE 21

Preparation of (2R,3R,4S)-6-nitro-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran The title compound (155 mg, 40%) was prepared in accordance with the same procedures as in Preparation Example 1, using the epoxide compound, (2R,3R,4R)-6-nitro-2-methyl-2-dimethoxymethyl-3,4-epoxy-3,4-dihydro-2H-1-benzopyran (200 mg, 0.71 mmol) and (4-trifluoromethoxyphenyl)(1H-imidazol-2-ylmethyl)amine 183 mg (0.71 mmol).

$^1$H NMR (200 MHz, CDCl$_3$) δ 1.49(s, 3H), 3.60(d, 6H), 4.20-4.50(m, 2H), 4.58-5.65(m, 2H), 5.18(s, 1H), 6.91-6.95 (m, 7H), 7.99(s, 1H), 8.04(dd, 1H).

PREPARATION EXAMPLE 22

Preparation of (2S,3S,4R)-6-cyano-4-[N-(4-chlorophenyl)-N-(1H-imidazol-2-ylmethyl)amino]-3-hydroxy-2-methyl-2-dimethoxymethyl-3,4-dihydro-2H-1-benzopyran The title compound (106 mg, 28%) was prepared in accordance with the same procedures as in Preparation Example 1, using the epoxide compound, (2S,3S,4S)-6-cyano-2-methyl-2-dimethoxymethyl-3,4-epoxy-3,4-dihydro-2H-1-benzopyran (210 mg, 0.8 mmol) and (4-chlorophenyl)(1H-imidazol-2-ylmethyl)amine (167 mg, 0.8 mmol).

$^1$H NMR (200 MHz, CDCl$_3$) δ 1.47(s, 3H), 3.58(s, 3H), 3.62(s, 3H), 4.35(m, 1H), 4.57(s, 1H), 5.16(br s, 1H), 6.81-6.93(m, 3H), 7.17(d, 1H), 7.38(s, 1H), 7.51(dd, 1H).

PREPARATION EXAMPLE 23

Preparation of (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran The nitro compound (521 mg, 1.07 mmol) prepared from Preparation Example 3 was dissolved in methanol (3 mL); and then 10% Pd/C (50 mg) was added thereto. The mixture was hydrogenated under 3 atmosphere pressure of H$_2$ for 12 hours. The reaction mixture was filtered through a Celite pad to remove a solid; and the filtrate was concentrated. The resulting residue was purified with silica gel column chromatography (methanol:dichloromethane=5:95) to give the title compound (368 mg, 75%).

$^1$H NMR (200 MHz, CDCl$_3$) δ 1.42(s, 3H), 3.61(s, 6H), 4.27(m, 2H), 4.42(s, 1H), 4.52(d, 1H), 5.24(m, 1H), 6.29(s, 1H), 6.58(d, 2H), 6.70(d, 2H), 6.98(m, 3H), 7.41(m, 2H).

PREPARATION EXAMPLE 24

Preparation of (2S,3S,4R)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran The nitro compound (177 mg, 0.36 mmol) prepared from Preparation Example 1 was dissolved in methanol (2 mL); and then a 0.4 M aqueous solution of Cu(OAc)$_2$ (0.38 mL, 0.15 mmol) was added thereto. Sodium borohydride (113 mg, 3.0 mmol) was slowly added at room temperature over 10 minutes to the reaction mixture. The reaction mixture was stirred for an hour; and then ethyl acetate (5 mL) was added thereto. The black precipitates were removed by filtration; and then a saturated aqueous solution of NaHCO$_3$ (5 mL) was added to the filtrate. The mixture was extracted with ethyl acetate (30 mL). The organic layer was washed with brine, dried over anhydrous sodium sulfate, and then concentrated in vacuo to remove the solvent. The resulting residue was purified with silica gel column chromatography (n-hexane:ethyl acetate=1:4) to give the title compound (58 mg, 35%).

$^1$H NMR (200 MHz, CDCl$_3$) δ 1.42(s, 3H), 3.61(s, 6H), 4.27(m, 2H), 4.52(d, 1H), 4.42(s, 1H), 5.24(m, 1H), 6.29(s, 1H), 6.58(d, 2H), 6.70(d, 2H), 6.98(m, 3H), 7.41(m, 2H).

PREPARATION EXAMPLE 25

Preparation of (2S,3S,4R)-6-amino-4-[N-(4-trifluoromethylphenyl)-N-(1H-imidazol-2-ylmethyl)amino]-3-hydroxy-2-methyl-2-dimethoxymethyl-3,4-dihydro-2H-1-benzopyran The title compound (34 mg, 57%) was prepared in accordance with the same procedures as in Preparation Example 24, using the nitro compound (65 mg, 0.12 mmol) prepared from Preparation Example 5.

¹H NMR (200 MHz, CDCl₃) δ 1.38(s, 3H), 3.60(s, 3H), 4.06-4.85(m, 3H), 4.41(s, 1H), 5.06(br s, 2H), 6.31(s, 1H), 6.57(d, 2H), 6.80-7.18(m, 7H)

PREPARATION EXAMPLE 26

Preparation of (2R,3R,4S)-6-amino-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran The title compound (23 mg, 24%) was prepared in accordance with the same procedures as in Preparation Example 23, using the nitro compound (100 mg, 0.19 mmol) prepared from Preparation Example 21.

¹H NMR (200 MHz, CDCl₃) δ 1.50(s, 3H), 3.60(d, 6H), 4.20-4.50(m, 2H), 4.59(s, 2H), 5.18(s, 1H), 6.30(s, 1H), 6.60(dd, 2H), 6.70-6.96(m, 6H)

PREPARATION EXAMPLE 27

Preparation of (2R,3R,4S)-6-amino-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran The title compound (19 mg, 15%) was prepared in accordance with the same procedures as in Preparation Example 23, using the nitro compound (135 mg, 0.28 mmol) prepared from Preparation Example 12.

¹H NMR (200 MHz, CDCl₃) δ 1.29(s, 3H), 2.27(s, 3H), 2.43(s, 3H), 3.60(s, 6H), 4.41-4.63(m, 5H), 6.57(dd, 1H), 6.70-7.19(m, 6H), 7.40(d, 1H)

PREPARATION EXAMPLE 28

Preparation of (2R,3R,4S)-6-amino-4-[N-(4-methoxyphenyl)-N-(1H-imidazol-2-ylmethyl)amino]-3-hydroxy-2-methyl-2-dimethoxymethyl-3,4-dihydro-2H-1-benzopyran The title compound (21 mg, 23%) was prepared in accordance with the same procedures as in Preparation Example 23, using the nitro compound (100 mg, 0.21 mmol) prepared from Preparation Example 14.

¹H NMR (200 MHz, CDCl₃) δ 1.36(s, 3H), 3.60(d, 6H), 3.64(s, 3H), 4.20-4.60(m, 3H), 4.45(s, 1H), 4.70-4.90(m, 2H), 6.50(m, 1H), 6.70(dd, 1H), 6.80-7.00(m, 6H), 7.40(d, 1H).

PREPARATION EXAMPLE 29

Preparation of (2R,3R,4S)-6-amino-4-[N-(4-bromophenyl)-N-(1H-imidazol-2-ylmethyl)amino]-3-hydroxy-2-methyl-2-dimethoxymethyl-3,4-dihydro-2H-1-benzopyran The title compound (50 mg, 53%) was prepared in accordance with the same procedures as in Preparation Example 23, using the nitro compound (100 mg, 0.19 mmol) prepared from Preparation Example 13.

¹H NMR (200 MHz, CDCl₃) δ 1.48(s, 3H), 3.61(d, 6H), 4.10-4.19(m, 2H), 4.22(s, 2H), 5.13(s, 1H), 6.33-7.15(m, 9H).

PREPARATION EXAMPLE 30

Preparation of (2S,3S,4R)-6-amino-4-[N-(2,3-dimethylphenyl)-N-(1H-imidazol-2-ylmethyl)amino]-3-hydroxy-2-methyl-2-dimethoxymethyl-3,4-dihydro-2H-1-benzopyran The title compound (35 mg, 54%) was prepared in accordance with the same procedures as in Preparation Example 23, using the nitro compound (70 mg, 0.14 mmol) prepared from Preparation Example 11.

¹H NMR (200 MHz, CDCl₃) δ 1.29(s, 3H), 2.27(s, 3H), 2.43(s, 3H), 3.60(s, 6H), 4.41-4.63(m, 5H), 6.57(dd, 1H), 6.70-7.19(m, 6H), 7.40(d, 1H).

PREPARATION EXAMPLE 31

Preparation of (2S,3S,4R)-6-amino-4-[N-(2-methoxyphenyl)-N-(1H-imidazol-2-ylmethyl)amino]-3-hydroxy-2-methyl-2-dimethoxymethyl-3,4-dihydro-2H-1-benzopyran The title compound (74 mg, 66%) was prepared in accordance with the same procedures as in Preparation Example 23, using the nitro compound (80 mg, 0.16 mmol) prepared from Preparation Example 16.

¹H NMR (200 MHz, CDCl₃) δ 1.30(s, 3H), 3.60(d, 6H), 3.80(s, 3H), 4.10-4.30(m, 2H), 4.45(s, 1H), 4.70-4.90(m, 2H), 6.50(dd, 1H), 6.70-7.00(m, 7H), 7.40(d, 1H).

PREPARATION EXAMPLE 32

Preparation of (2S,3S,4R)-6-amino-4-[N-(4-methoxyphenyl)-N-(1H-imidazol-2-ylmethyl)amino]-3-hydroxy-2-methyl-2-dimethoxymethyl-3,4-dihydro-2H-1-benzopyran The title compound (74 mg, 77%) was prepared in accordance with the same procedures as in Preparation Example 23, using the nitro compound (103 mg, 0.21 mmol) prepared from Preparation Example 6.

¹H NMR (200 MHz, CDCl₃) δ 1.36(s, 3H), 3.60(d, 6H), 3.64(s, 3H), 4.20-4.60(m, 3H), 4.45(s, 1H), 4.70-4.90(m, 2H), 6.50(m, 1H), 6.70(dd, 1H), 6.80-7.00(m, 6H), 7.40(d, 1H).

PREPARATION EXAMPLE 33

Preparation of (2S,3S,4R)-6-amino-4-[N-(2,4-dimethylphenyl)-N-(1H-imidazol-2-ylmethyl)amino]-3-hydroxy-2-methyl-2-dimethoxymethyl-3,4-dihydro-2H-1-benzopyran The title compound (54 mg, 67%) was prepared in accordance with the same procedures as in Preparation Example 23, using the nitro compound (86 mg, 0.18 mmol) prepared from Preparation Example 9.

$^1$H NMR (200 MHz, CDCl$_3$) δ 1.26(s, 3H), 2.20(s, 3H), 2.43(s, 3H), 3.58(s, 6H), 4.36-4.54(m, 3H), 4.60(m, 2H), 6.56(dd, 1H), 6.70(dd, 1H), 6.80-7.15(m, 6H), 7.36(d, 1H).

PREPARATION EXAMPLE 34

Preparation of (2S,3S,4R)-6-amino-4-[N-(2-isopropylphenyl)-N-(1H-imidazol-2-ylmethyl)amino]-3-hydroxy-2-methyl-2-dimethoxymethyl-3,4-dihydro-2H-1-benzopyran The title compound (30 mg, 73%) was prepared in accordance with the same procedures as in Preparation Example 23, using the nitro compound (45 mg, 0.09 mmol) prepared from Preparation Example 10.

$^1$H NMR (200 MHz, CDCl$_3$) δ 1.22-1.29(m, 9H), 3.60(d, 6H), 4.10-4.62(m, 5H), 6.50-6.77(m, 2H), 6.85-7.30(m, 6H), 7.60(m, 1H).

PREPARATION EXAMPLE 35

Preparation of (2S,3S,4R)-6-amino-4-[N-(4-trifluoromethoxyphenyl)-N-(1H-imidazol-2-ylmethyl)amino]-3-hydroxy-2-methyl-2-dimethoxymethyl-3,4-dihydro-2H-1-benzopyran The title compound (34 mg, 72%) was prepared in accordance with the same procedures as in Preparation Example 23, using the nitro compound (50 mg, 0.10 mmol) prepared from Preparation Example 7.

$^1$H NMR (200 MHz, CDCl$_3$) δ 1.50(s, 3H), 3.60(d, 6H), 4.20-4.50(m, 2H), 4.59(s, 2H), 5.18(s, 1H), 6.30(s, 1H), 6.60(dd, 2H), 6.70-6.96(m, 6H).

PREPARATION EXAMPLE 36

Preparation of (2S,3S,4R)-6-amino-4-[N-(4-bromophenyl)-N-(1H-imidazol-2-ylmethyl)amino]-3-hydroxy-2-methyl-2-dimethoxymethyl-3,4-dihydro-2H-1-benzopyran The title compound (41 mg, 88%) was prepared in accordance with the same procedures as in Preparation Example 23, using the nitro compound (50 mg, 0.10 mmol) prepared from Preparation Example 8.

$^1$H NMR (200 MHz, CDCl$_3$) δ 1.48(s, 3H), 3.61(d, 6H), 4.10-4.19(m, 2H), 4.22(s, 2H), 5.13(s, 1H), 6.33-7.15(m, 9H).

PREPARATION EXAMPLE 37

Preparation of (2S,3S,4R)-6-amino-4-[N-(4-fluorophenyl)-N-(1H-imidazol-2-ylmethyl)amino]-3-hydroxy-2-methyl-2-dimethoxymethyl-3,4-dihydro-2H-1-benzopyran The title compound (44 mg, 95%) was prepared in accordance with the same procedures as in Preparation Example 23, using the nitro compound (50 mg, 0.10 mmol) prepared from Preparation Example 15.

$^1$H NMR (200 MHz, CDCl$_3$) δ 1.49(s, 3H), 3.60(d, 6H), 4.30(m, 4H), 4.98(s, 1H), 6.33(s, 1H), 6.55(dd, 2H), 6.60-6.92(m, 6H).

EXAMPLE 1

Evaluation of Inhibitory Effects Against Angiogenesis in Animal Models Having Corneal Damage The tests were performed by using Sprague Dawley rats (8 weeks old, male) as animals having corneal damage (15 rats for the experiment group; and 1 rat for normal group, respectively). The corneal damage was induced by applying a cotton swab coated with silver nitrate to the surface of the rat corneas, as as to induce a damage having a diameter of 2 mm in the central cornea. On the third day after inducing the corneal damages, we confirmed the establishment of corneal angiogenesis-inducing models and then subconjunctivally injected a solution (20 μl) prepared by dissolving the compound of Preparation Example 23, i.e., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran (KR-31831) in phosphate buffered saline (PBS) containing 10% PEG 400, in the concentration of 0.3 mg/ml. In case of the control group, the PBS (20 μl) containing 10% PEG 400 was subconjunctivally injected. As a positive control, a solution (20 μl) prepared by dissolving Avastin (used as an angiogenesis inhibitor) in PBS in the concentration of 10 mg/ml was subconjunctivally injected. 1 week after the drug administrations, the photographs of the corneal angiogenesis were shown in FIG. 1. The evaluations quantifying the photographs of FIG. 1 were performed by using the Image J (NIH, USA) program and the results thereof were shown in FIG. 2.

Figure 2:
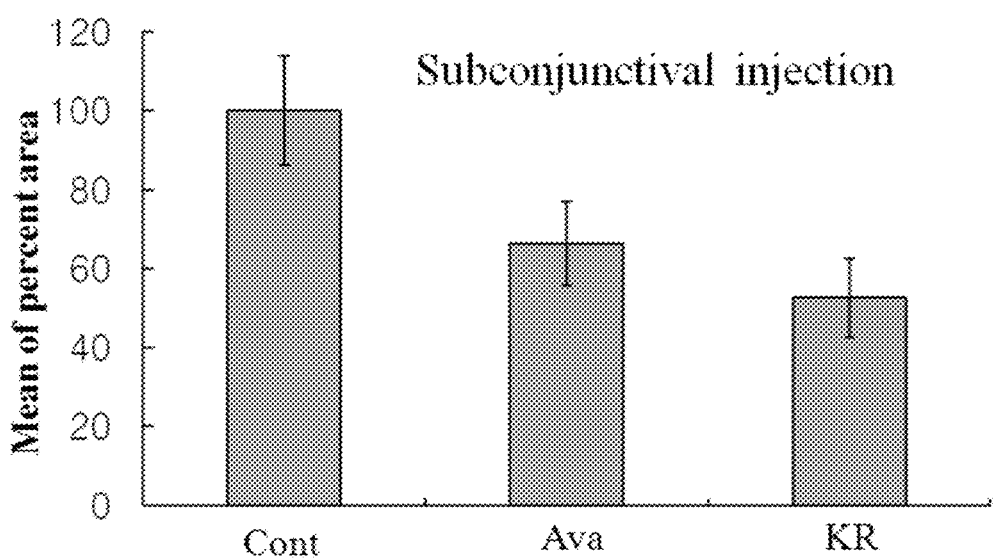
FIGS. 2 and 3 are the results (graphs) obtained by evaluating inhibitory effects against corneal angiogenesis in animal models with corneal damage.

As shown in FIG. 1, the animal models injected with the compound of the present invention showed lower corneal angiogenesis than the control group injected with PBS and the positive group injected with Avastin. And also, as shown in FIG. 2, the group administered with the compound of the present invention (KR) and the group administered with Avastin (Ava) respectively showed 52.6±10% and 66.4±10.6% of corneal angiogenesis, in comparison with the corneal angiogenesis (100%) of the control group (Cont). Therefore, it can be seen that, even when the compound of the present invention was administered in lower concentration than Avastin, it has superior inhibitory effect against corneal angiogenesis (FIG. 2).

EXAMPLE 2

Evaluation of Inhibitory Effects Against Angiogenesis in Animals Model Having Corneal Damage Except for performing both the subconjunctval injection and the eye drop-administration of (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran and Avastin, the inhibitory effects against angiogenesis were evaluated according to the same manners as in Example 1. For the subconjunctval injection, we used a solution (20 μl) prepared by dissolving (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran in PBS containing 10% PEG 400, in the concentration of 0.3 mg/ml, and a solution (20 μl) prepared by dissolving Avastin in PBS in the concentration of 10 mg/ml. And also, for the eye drop-administration, we used each solution (50 μl, one drop) prepared by dissolving each drug in PBS containing 30% by weight of PEG (polyethylene glycol 400) and 10% by weight of DMSO (dimethyl sulfoxide) in the same concentrations thereof as mentioned in the above; and then adjusting the pH of the resulting solution to pH 7 with hydrochloric acid. The results thereof are shown in FIG. 3.

Figure 3:
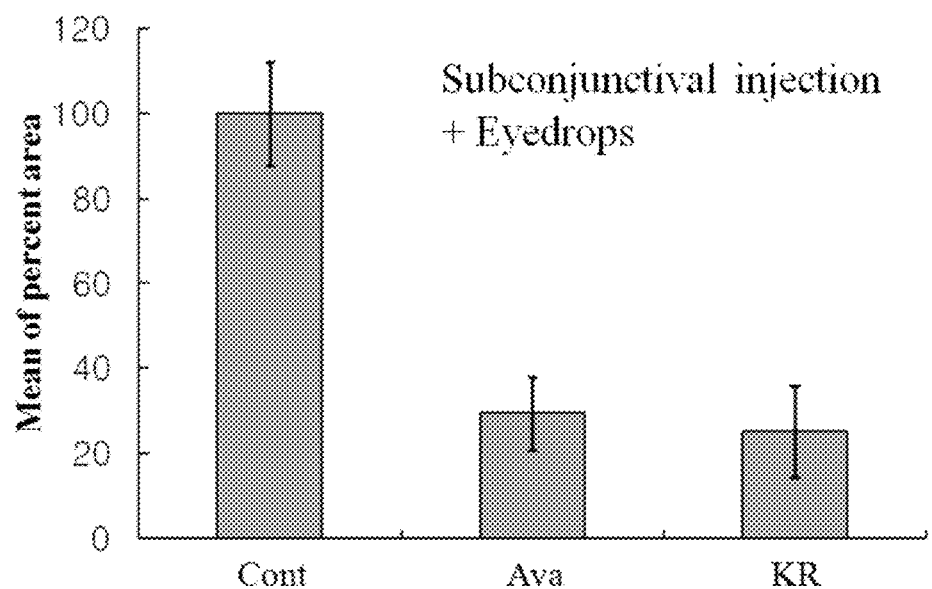

As shown in FIG. 3, in comparison with the angiogenesis (100%) of the control group (Cont), 29.3±8.6% of angiogenesis was shown in case of the group administered with Avastin (Ava); and 25.1±10.8% of angiogenesis was shown in case of the group administered with the compound of the present invention (KR). It can be seen that, even when the compound of the present invention was used in lower concentration than Avastin, it has superior inhibitory effect against angiogenesis (FIG. 3), which is the same as in Example 1.

EXAMPLE 3

Measurement of the Expression of a VEGF Receptor 2 (FLK-1)

The tests were performed for confirming corneal angiogenesis as a marker. To a Trizole™ solution (200 μl), were added each corneal tissue obtained from the rats of Example 1. Total RNAs were isolated and then cDNAs were prepared by using a reverse transcriptase. Each cDNA (5 μl) was mixed with the primer set of FLK-1 and then PCR amplification was performed in a thermocycler under the following conditions; denaturation at 94° C. for 5 minutes, and then 35 cycles of denaturation at 94° C. for 20 seconds, annealing at 58° C. for 1 minute, and extension at 72° C. for 25 seconds. Each PCR product was loaded on 1% agarose gel; and the resulting ethidium bromide fluorescent bands were identified. The results thereof were shown in FIG. 4.

Figure 4:
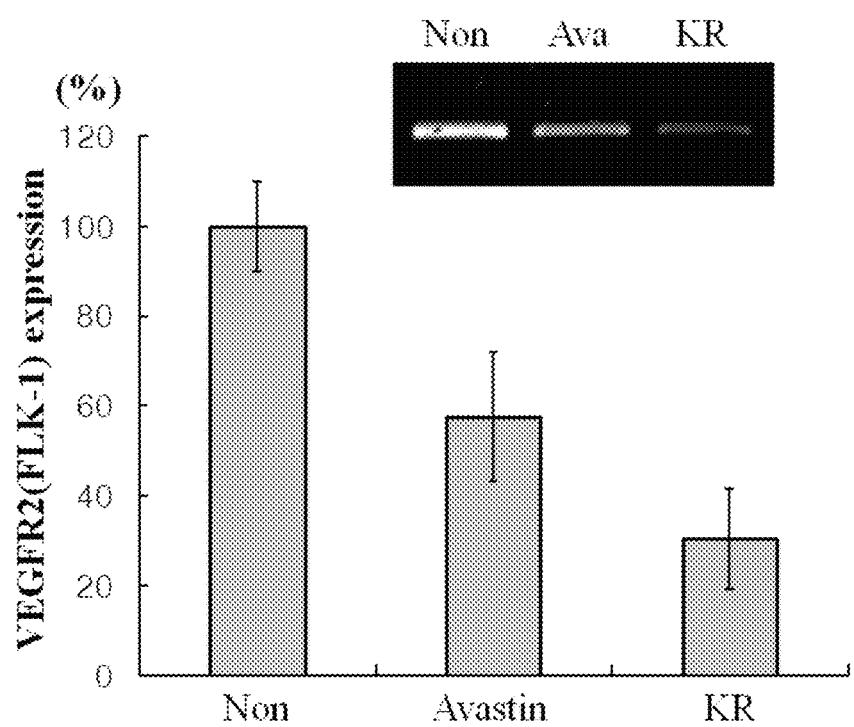
FIG. 4 is the results obtained by evaluating inhibitory effects against expression of the VEGF receptor 2 (FLK-1).

As shown in FIG. 4, it can be seen that the group (KR) subconjunctivally injected with a solution (20 μl) of the compound of the present invention, i.e., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran in the concentration of 0.3 mg/ml showed remarkably low (about 30%) FLK-1 expression in the cornea, in comparison with the FLK-1 expression in the cornea (100%) in case of the control group (Non) injected with PBS (20 μl) and the FLK-1 expression in the cornea (about 59%) in case of the group (Avastin) injected with Avastin (20 μl) in the concentration of 10 mg/ml

EXAMPLE 4

Evaluation of Effects on Normal Regeneration of Corneal Epithelial Cells in Animal Models Animal models having damage in the corneal epithelial cells were established by anesthetizing rats (8 weeks old, 200 g to 250 g) with a mixed solution of rompun and zoletil (1 ml/kg) and then scraping the corneal epithelial cells at the center of the cornea in a circular form having 2 mm diameter with a surgical knife. The removal of corneal epithelial cells was confirmed with a 1% fluorescein solution. The eye drop formulation (50 μl) used in Example 2 was administered twice a day, i.e., every 12 hours. The corneas at 0 hour, 18 hours, 36 hours after the administration were shown in FIG. 5. The evaluations quantifying the photographs of FIG. 5 were performed by using the Image J (NIH, USA) program and the results thereof were shown in FIG. 6.

Figure 5:
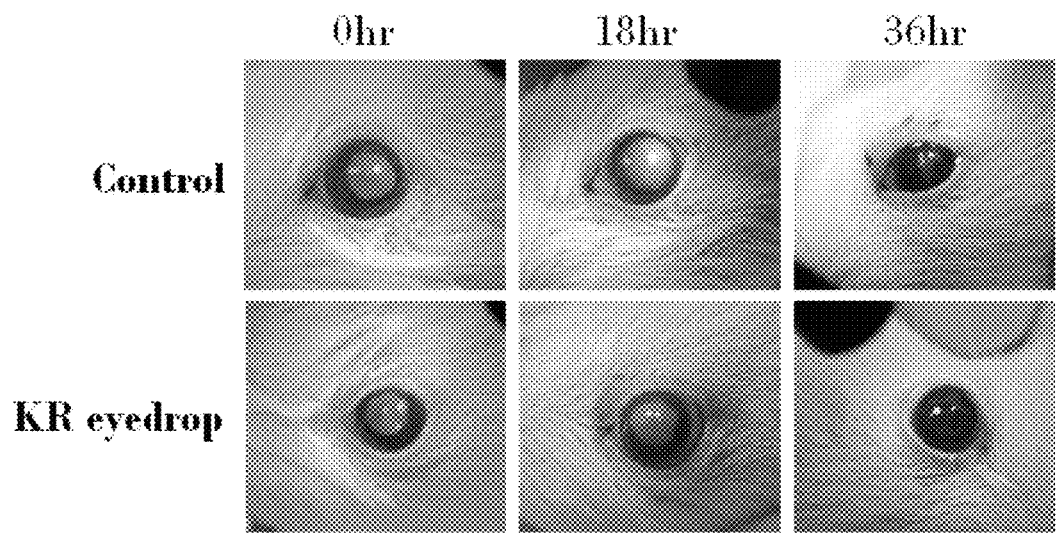
FIG. 5 is the results (photographs) obtained by evaluating effects on normal regeneration of the corneal epithelial cells.
Figure 6:
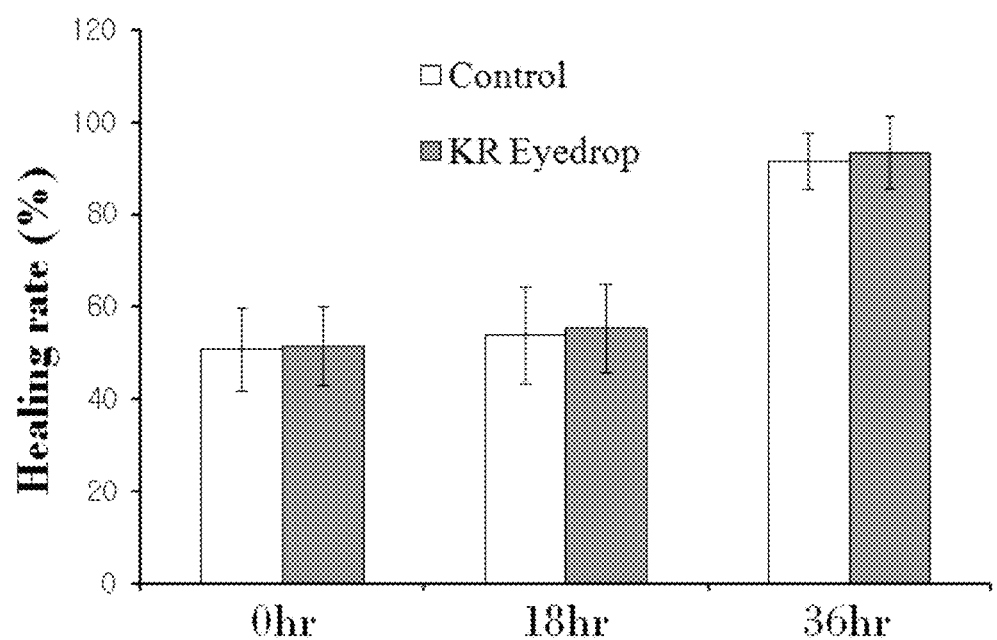
FIG. 6 is the results (graphs) obtained by evaluating effects on normal regeneration of the corneal epithelial cells.

As shown in FIGS. 5 and 6, when each corneal epithelial damage size was compared with the whole cornea, the control group (Control) showed 51±9% of healing rate at 0 hour after the administration, 54±10% of healing rate at 18 hours after the administration, and 92±6% of healing rate at 36 hours after the administration, respectively; and the group (KR eyedrop) administered with the eye drop formulation containing the compound of the present invention, i.e., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran, showed 52±9% of healing rate at 0 hour after the administration, 55±9% of healing rate at 18 hours after the administration, and 94±8% of healing rate at 36 hours after the administration, respectively. Therefore, it can be seen that the normal healing rate of corneal epithelial cells is not inhibited by the eye drop formulation containing the compound of the present invention.

EXAMPLE 5

Observation of Therapeutic Effects of Macular Degeneration in Animal Models Having Retinal Damage The tests were performed by using Brown Norway rats (8 weeks old, male) as animals having retinal damage (15 rats for the experiment group; and 1 rat for normal group, respectively). The retinal Bruch's membrane of each Brown Norway rat was damaged using a Zeiss 532s laser at the intensity of 200 mV, 30 ms. On the third day after the laser-damaging, the drug was administered into the vitreous humor in order to observe the retinal vessels. The compound of the present invention, i.e., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran was administered with the solutions (10 μl of each solution) obtained by dissolving in PBS containing 30% PEG 400 and 10% DMSO, in the concentrations of 0.1 mg/ml and 0.3 mg/ml. Avastin was administered with the solution (10 μl) obtained by dissolving in PBS in the concentration of 2.5 mg/ml. In case of the control group, the PBS (10 μl) was administered. In addition, (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran was intraperitoneally administered with the solution obtained by dissolving in PBS containing 30% PEG 400 and 10% DMSO, in the dose of 25 mg/kg. 2 weeks after the drug administrations, dextran-FITC was injected into the left ventricle in the dose of 25 mg/kg, followed by enucleating the eye after 5 minutes therefrom; and then fixing in a 10% formalin solution. The cornea and the eye lens were removed from the fixed eye, which was then observed under a fluorescence microscope. Angiogenesis was identified by the intensity and leakage of dextran-FITC in the laser-induced damage site; and the results thereof were shown in FIG. 7. The evaluations quantifying the photographs of FIG. 7 were performed by using the Image J (NIH, USA) program and the results thereof were shown in FIG. 8.

Figure 7:
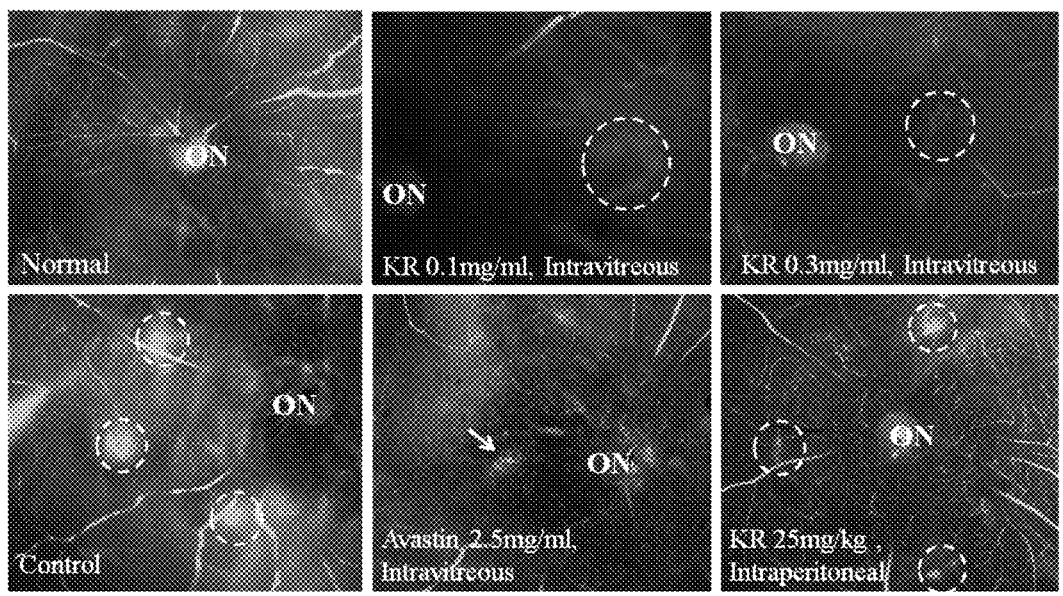
FIG. 7 is the results (photographs) obtained by evaluating inhibitory effects against retinal angiogenesis in Brown Norway rats.

As shown in FIG. 7, a reticulate form were observed in the normal retinal vessels (Normal) by the dextran-FITC staining, while the leakage of dextran-FITC in the laser-induced damage site was observed in case of the control group (Control). However, it can be seen that, in case of the group administered with the compound of the present invention, the leakage area of dextran-FITC in the laser-induced damage site was reduced in comparison with the control group and the Avastin-administered group.

Figure 8:
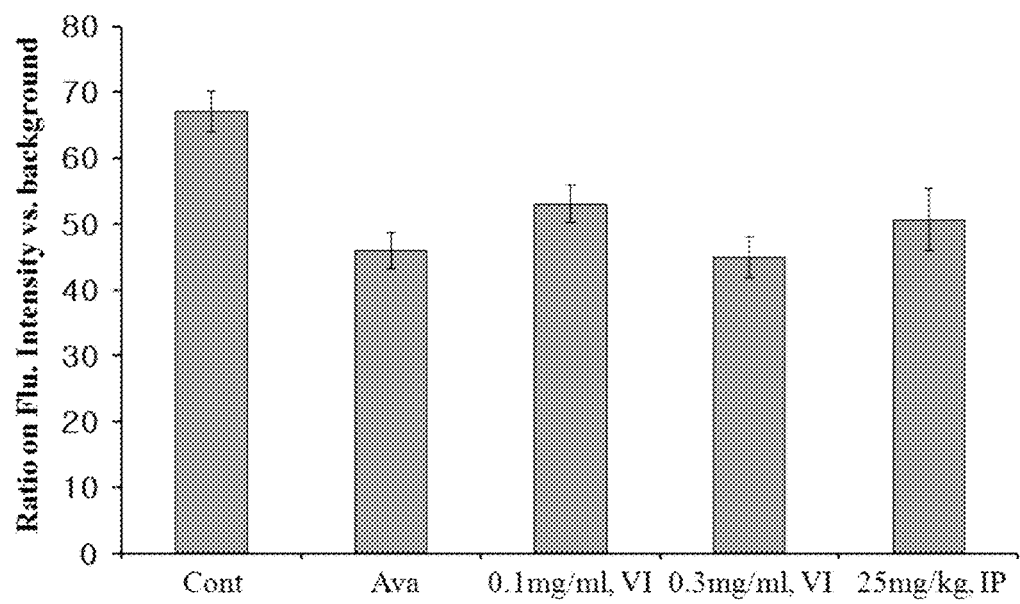
FIG. 8 is the results (graphs) obtained by evaluating inhibitory effects against retinal angiogenesis in Brown Norway rats.

FIG. 8 shows the evaluation results through quantifying the fluorescence intensities in the photographs of FIG. 7. When the fluorescence intensity of the surrounding vessels was 100, the control group (Control) administered with a sterile saline showed 67±3 of fluorescence intensity; and the group administered with Avastin (Ave) showed 46±3 of fluorescence intensity. In contrast, among the groups administered with the compound of the present invention, the 0.1 mg vitreous humor-administered group (0.1 mg/ml, VI) showed 53±2.8 of fluorescence intensity; the 0.3 mg vitreous humor-administered group (0.3 mg/ml, VI) showed 45±3.1 of fluorescence intensity; and the intraperitoneally administered group (25 mg/kg, IP) showed 51±5 of fluorescence intensity. Therefore, it can be seen that the groups administered with the compound of the present invention showed remarkably low fluorescence intensity; and that, even when the compound of the present invention was injected in lower concentration than Avastin known as an angiogenesis inhibitor, it has equivalent or more effects. In addition, from the results that the intraperitoneal administration also showed the therapeutic effects, it can be seen that the efficiency in terms of administration method is higher in comparison with the conventional therapeutic agent.

EXAMPLE 6

Measurement of Therapeutic Effects of Macular Degeneration in Animal Models Having Retinal Damage The tests were performed by using Yutacan Micro pigs (3 kg, male) as animal models having retinal damage (15 pigs for the experiment group). The retinal macular degeneration models were established according to the same procedures as in Brown Norway rats of Example 5. The eye drop formulation (100 μl, 0.9 mg/ml) prepared according to the same procedures as in Example 2 was administered four times per day for 2 weeks. For vitreous injection, the solution of the same compound (20 μl, 0.3 mg/ml) was injected into the vitreous humor once. 2 weeks after the administrations, 1% fluorescein was intravenously injected so as to observe the laser-induced damage site; and the effects of the compound of the present invention, i.e., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran. The results were shown in FIG. 9. The evaluations quantifying the photographs of FIG. 9 were performed by using the Image J (NIH, USA) program and the results thereof were shown in FIG. 10.

Figure 9:
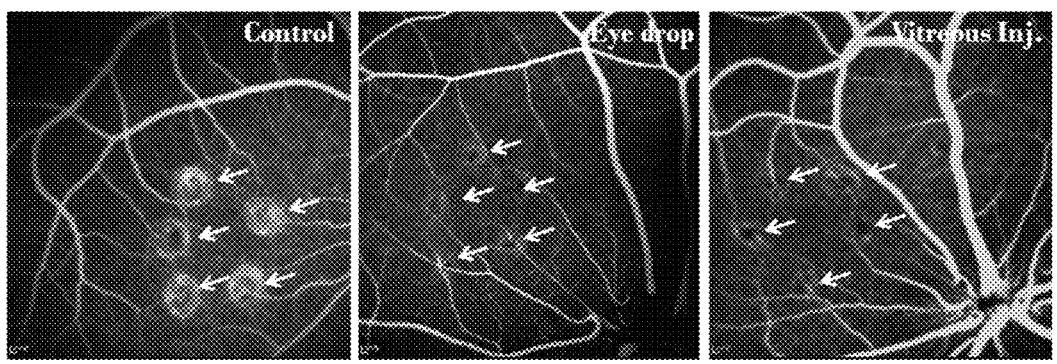
FIG. 9 is the results (photographs) obtained by evaluating inhibitory effects against retinal angiogenesis in micro pigs.
Figure 10:
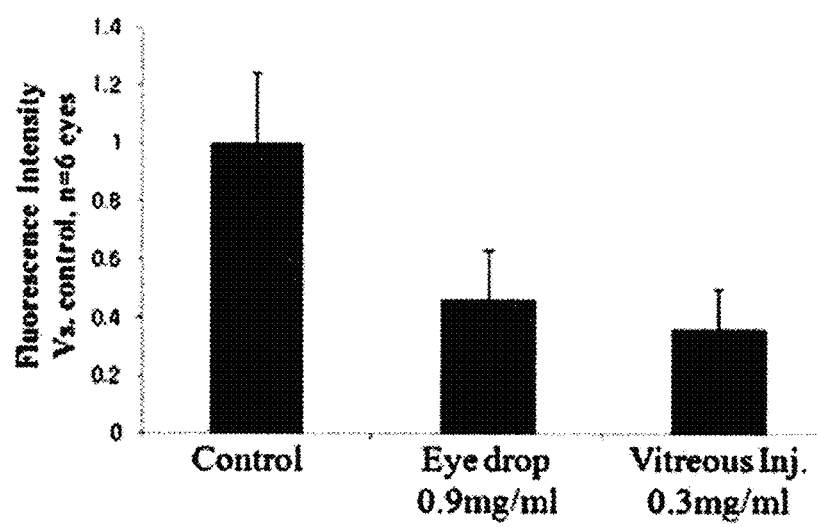
FIG. 10 is the results (graphs) obtained by evaluating inhibitory effects against retinal angiogenesis in micro pigs.

As shown in FIGS. 9 and 10, when the intensity of the non-drug administered control group was 1, the eye drop formulation-administered group (4 times per day, 2 weeks) (Eye drop) showed 0.46±0.17 of intensity; and the vitreously-administered group (Vitreous Inj.) showed 0.36±0.14 of intensity. Therefore, the compound of the present invention is effective for the treatment of macular degeneration. Especially, it can be seen that, even when the compound of the present invention is administered in the eye drop formulation form, it shows an excellent therapeutic effect of macular degeneration.

EXAMPLE 7

Measurement of Retinal Delivery of Eye Drop Formulation in Animal Models

We evaluated whether the eye drop formulation containing (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran is penetrated through the cornea and then delivered to the retina. Brown Norway rats (8 weeks old) were used in the test; and the animal models were established according to the same procedures as in Example 5. The eye drop formulations (100 μl of each formulation) of the following Formulation Examples 1 to 3 (i.e., the eye drop formulations in the solution form of Formulation Examples 1 and 2; and the eye drop formulation in the suspension form of Formulation Example 3) were administered four times per day for 2 weeks, respectively. 2 weeks after the administrations, 1% fluorescein was intravenously injected so as to observe the laser-induced damage site; and the effects of the compound of the present invention, i.e., (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran. The results were shown in FIG. 11. The evaluations quantifying the photographs of FIG. 11 were performed by using the Image J (NIH, USA) program and the results thereof were shown in FIG. 12.

Figure 11:
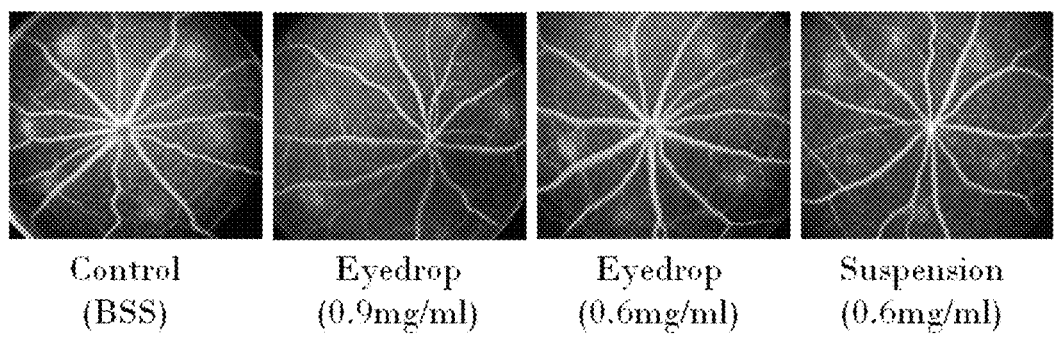
FIG. 11 is the results (photographs) obtained by evaluating inhibitory effects of the eye drop solution and the eye drop suspension against retinal angiogenesis.
Figure 12:
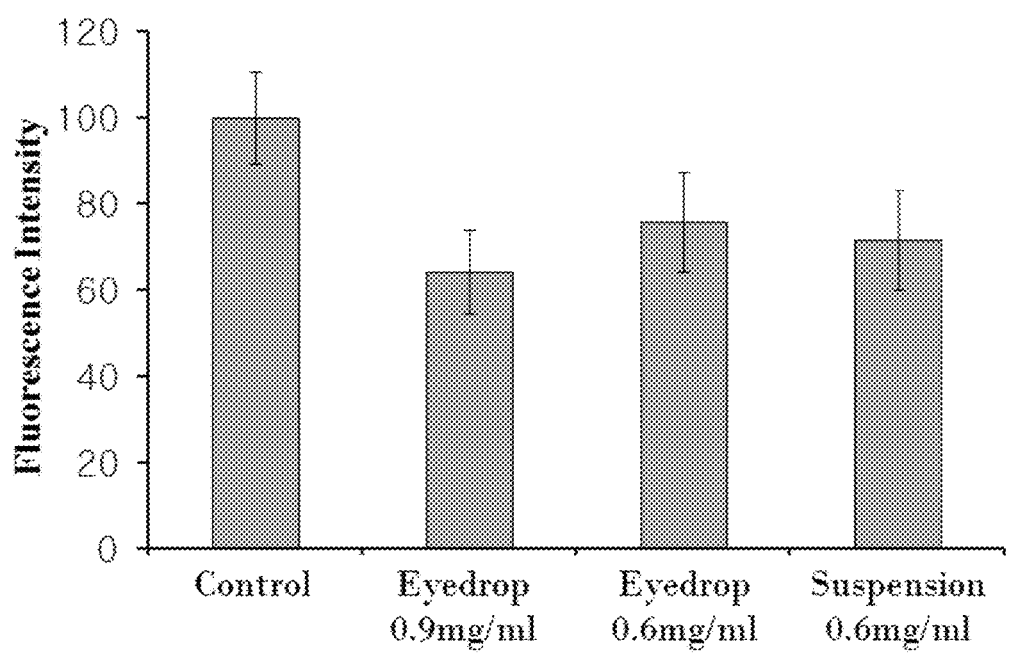
FIG. 12 is the results (graphs) obtained by evaluating inhibitory effects of the eye drop solution and the eye drop suspension against retinal angiogenesis.

As shown in FIGS. 11 and 12, when the intensity of the non-drug administered control group was 100%, the group administered with the eye drop formulation in the solution form having the concentration of 0.9 mg/ml (Eyedrop 0.9 mg/ml) showed 64.3±9.7% of intensity; the group administered with the eye drop formulation in the solution form having the concentration of 0.6 mg/ml (Eyedrop 0.6 mg/ml) showed 75.8±11.6% of intensity; and the group administered with the eye drop formulation in the suspension form having the concentration of 0.6 mg/ml (Suspension 0.6 mg/ml) showed 71.57±11.58% of intensity. Therefore, it can be seen that, even when the eye drop formulations prepared according to the present invention were externally and topically administered, those show excellent therapeutic effects of macular degeneration.

EXAMPLE 8

Measurement of Retinal Delivery of Eye Drop Formulation in Animal Models

We evaluated whether the eye drop formulation containing (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran is penetrated through the cornea and then delivered to the retina. Rats (8 weeks old) were used in the test; and the eye drop formulation (50 μl) prepared in the following Formulation Example 1 was dropped on each rat's eye. The delivery level of the compound to the retina was measured; and the results thereof are shown in the following table 1.

TABLE 1

| Time | Aqueous humor | Vitreous humor | Retina | Plasma |
|---|---|---|---|---|
| 30 minutes | 1250 ng/ml | 195 ng/ml | 846 ng/ml | N.D. |
| 120 minutes | 827 ng/ml | 194 ng/ml | 225 ng/ml | 0.9 ng/ml |

N.D.: not detected

As shown in the above table 1, the compound was detected in the levels of 1250 ng/ml in the aqueous humor, 195 ng/ml in the vitreous humor, and 846 ng/ml in the retina, respectively, 30 minutes after the administration. 120 minutes after the administration, the compound was detected in the levels of 827 ng/ml in the aqueous humor, 194 ng/ml in the vitreous humor, and 225 ng/ml in the retina, respectively. In the plasma, the compound was not detected, 30 minutes after the administration; and was detected in the level of 0.9 ng/ml, 120 minutes after the administration. Therefore, it can be seen that, when the compound of the present invention was dropped on the eye, it is delivered to the retina; and that only a negligible amount is absorbed into the blood.

The compound of Formula 1 or its salt according to the present invention may be formulated into various dosage forms according to the purposes, preferably into an eye drop formulation form. The eye drop formulation may be in a solution form or in a suspension form. The following Formulation Examples illustrate representative examples of the eye drop formulations in a solution or suspension form, but the present invention is not limited thereto.

FORMULATION EXAMPLES 1 and 2

Preparation of Eye Drop Formulations in the Solution Form

The eye drop formulations in the solution form were prepared according to the components and amounts shown in Table 2. Each amount of Table 2 represents the amount thereof per 1 ml of total volume. The compound of Preparation Example 23, polyethylene glycol 400, glycerin, EDTA, and boric acid were dissolved in sterile water. The pH was adjusted to 6.5±0.5 with diluted hydrochloric acid; and then sterile water was added to the solution, so as to adjust the total volume.

TABLE 3

| Component | Formulation Example 1 | Formulation Example 2 |
|---|---|---|
| The compound of Formula 1 (Preparation Example 23) | 0.9 mg | 0.6 mg |
| Polyethylene glycol 400 | 150 mg | 150 mg |
| Glycerin | 120 mg | 120 mg |
| EDTA | 0.5 mg | 0.5 mg |
| Boric acid | 10 mg | 10 mg |
| Diluted hydrochloric acid | q.s. | q.s. |

FORMULATION EXAMPLE 3

Preparation of Eye Drop Formulation in the Suspension Form

The eye drop formulation in the suspension form was prepared according to the components and amounts shown in Table 3. Each amount of Table 3 represents the amount thereof per 1 ml of total volume. The compound of Preparation Example 23, povidone K-25, EDTA, boric acid, Borax, and sodium chloride were dispersed in sterile water. The pH was adjusted to 7.0±0.5 with diluted hydrochloric acid; and then sterile water was added to the suspension, so as to adjust the total volume.

TABLE 3

| Component | Formulation Example 3 |
|---|---|
| The compound of Formula 1 (Preparation Example 23) | 0.6 mg |
| Povidone K-25 | 20 mg |
| EDTA | 0.5 mg |
| Boric acid | 10 mg |
| Borax | 1 mg |
| Sodium chloride | 2 mg |
| Diluted hydrochloric acid | q.s. |

EXPERIMENTAL EXAMPLE 1

Corneal Wound Healing Assay (1)

1. Animals

SD rats (male, 8 weeks, 250 g) were used. Animal study protocol was in accordance with the Association for Research in Vision and Ophthalmology Statement for the Use of Animals in Ophthalmic and Visual Research. All animals were housed in individual cages and maintained under standard conditions (12 hour light-dark cycle).

2. Corneal Epithelium Removal

Rats were anesthetized by Zoletil® (50 mg/kg, Tiletamina 25 mg, Zolazepam 25 mg; Vibrac, Carros, France) and Rompun® (10 mg/kg, Bayer, France). The cornea was anesthetized by topical 0.5% proparacaine (Alcaine®; Alcon, Fort Worth, Tex., USA). After applying 0.5% proparacaine drops, 5.0 mm Trephine Blade® (Katena, Denville, N.J., USA) was placed and fixed firmly on the corneal surface. One drop of 20% ethanol were put into the tephine well and left in place for 30 seconds, then absorbed with a dry cellulose sponge (Merocel®; Medtronic Solan, Jacksonville, Fla., USA) and irrigated with normal saline. And the epithelium was removed in 6.0 mm diameter.

3. Drugs Tested i. KR-31831 [(2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran];

ii. TG100801 as disclosed in J. Med. Chem. Vol. 51, pages 1546-1559, 2008;

iii. ATG-003 as disclosed in US 2007/0167526;

iv. Pazopanib as disclosed in WO 2007/064752; and v. Vehicle as control;

4. Drug Treatment

The drugs were each topically applied in 10 mg/ml (1%) concentration (in 5% DMSO, 10% PEG (Mw 400) and 85% saline (0.9% NaCl)) in every 6 hour.

5. Analysis:

The epithelial wounds were visualized using 1% fluorescein sodium solution, and the cornea was observed at 0 and 18 hours from corneal epithelium removal, respectively. The corneal wounds were captured by digital camera under cobalt blue light and the defect area was analyzed by Image J software (Ver 4.1, NIH). The significance between Vehicle and each group was analyzed by paired T-test, and the significance of the test was analyzed by One Way ANOVA analysis.

Figure 13:
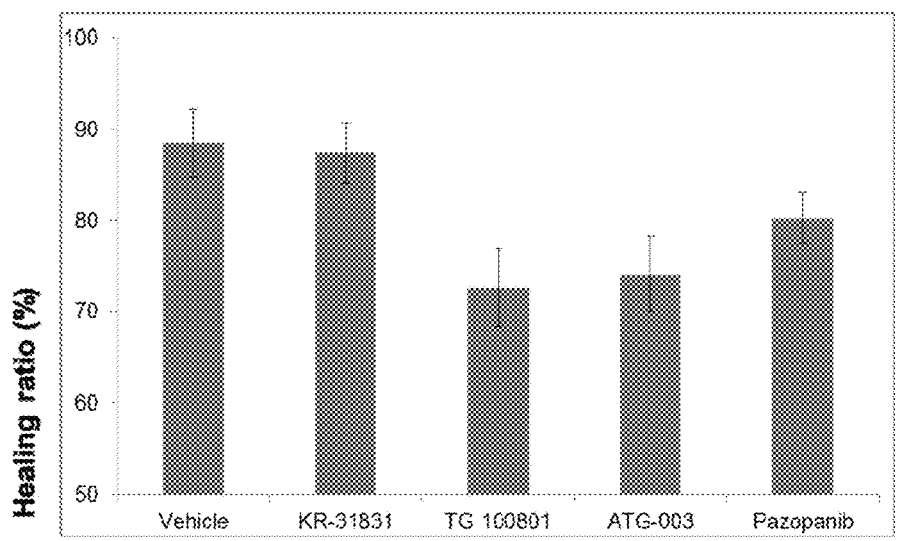
FIG. 13 is the results obtained by evaluating the effects on normal regeneration of the corneal epithelial cells, when the test compounds were administered in the concentration of 10 mg/ml.
Figure 13:
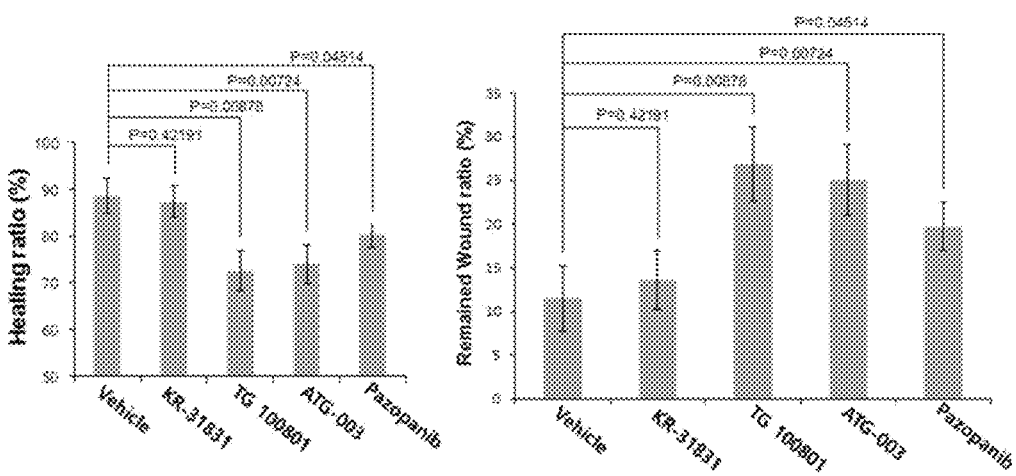

6. Results:

Inhibitory effect of the anti-angiogenic drugs on normal healing of corneal wound is shown in FIG. 13. As shown in FIG. 13, TG100801, ATG-003 and Pazopanib showed inhibitory effect on normal healing of rat corneal epithelial wound when administered in the concentration of 10 mg/ml. That is, compared to vehicle-administered corneal eithelial (control) and compared to KR-31831, the TG 100801-administered corneal epithelial showed the lowest rate (%)

of wound healing (=the highest inhibition on normal wound healing), the ATG-003-administered corneal epithelial showed the second lowest rate (%) of wound healing (=the second highest inhibition on normal wound healing), and the Pazopanib-administered corneal epithelial showed the least lowest rate (%) of wound healing among the three but lower than the control (=the lowest inhibition on normal wound healing but higher than control). (p=0.00000191).

EXPERIMENTAL EXAMPLE 2

Corneal Wound Healing Assay (2)

1. Animals

SD rats (male, 8 weeks, 250 g) were used. Animal study protocol was in accordance with the Association for Research in Vision and Ophthalmology Statement for the Use of Animals in Ophthalmic and Visual Research. All animals were housed in individual cages and maintained under standard conditions (12 hour light-dark cycle).

2. Corneal Epithelium Removal

Rats were anesthetized by Zoletil® (50 mg/kg, Tiletamina 25 mg, Zolazepam 25 mg; Vibrac, Carros, France) and Rompun® (10 mg/kg, Bayer, France). The cornea was anesthetized by topical 0.5% proparacaine (Alcaine®; Alcon, Fort Worth, Tex., USA). After applying 0.5% proparacaine drops, 5.0 mm Trephine Blade® (Katena, Denville, N.J., USA) was placed and fixed firmly on the corneal surface. One drop of 20% ethanol were put into the tephine well and left in place for 30 seconds, then absorbed with a dry cellulose sponge (Merocel®; Medtronic Solan, Jacksonville, Fla., USA) and irrigated with normal saline. And the epithelium was removed in 6.0 mm diameter.

3. Drugs Tested i. KR-31831 [(2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran];
ii. TG100801 as disclosed in J. Med. Chem. Vol. 51, pages 1546-1559, 2008;
iii. ATG-003 as disclosed in US 2007/0167526;
iv. Pazopanib as disclosed in WO 2007/064752; and
v. Vehicle as control;

4. Drug Treatment

The drugs were each topically applied in 3 mg/ml (0.3%) and 6 mg/ml (0.6%) concentrations (in 5% DMSO, 10% PEG (Mw 400) and 85% saline (0.9% NaCl)) in every 6 hour, respectively.

5. Analysis:

The epithelial wounds were visualized using 1% fluorescein sodium solution, and the cornea was observed at 0 and 18 hours from corneal epithelium removal, respectively. The corneal wounds were captured by digital camera under cobalt blue light and the defect area was analyzed by Image J software (Ver 4.1, NIH). The significance between Vehicle and each group was analyzed by paired T-test, and the significance of the test was analyzed by One Way ANOVA analysis.

Figure 14:
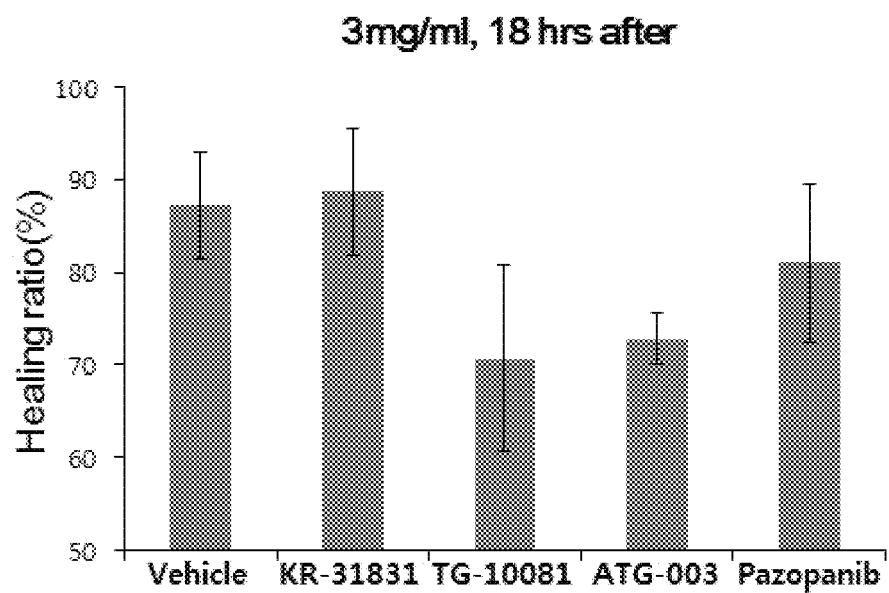
FIG. 14 is the results obtained by evaluating the effects on normal regeneration of the corneal epithelial cells, when the test compounds were administered in the concentration of 3 mg/ml.
Figure 15:
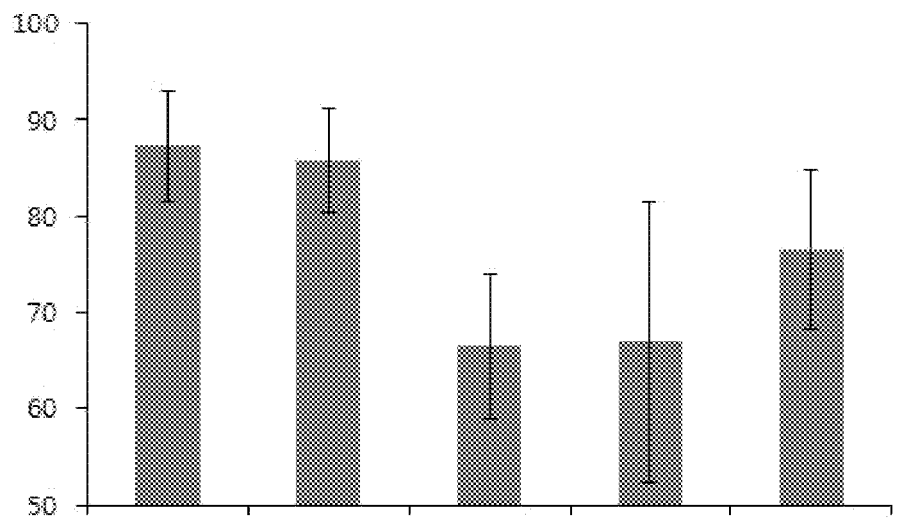
FIG. 15 is the results obtained by evaluating the effects on normal regeneration of the corneal epithelial cells, when the test compounds were administered in the concentration of 6 mg/ml.

6. Results:

Inhibitory effect of the anti-angiogenic drugs on normal healing of corneal wound is shown in FIGS. 14 and 15. As shown in FIGS. 14 and 15, TG100801, ATG-003 and Pazopanib showed inhibitory effect on normal healing of rat corneal epithelial wound when administered in the concentrations of 3 and 6 mg/ml, which is similar to the results when administered in the concentration of 10 mg/ml. However, KR-31831 did not show inhibitory effect on normal healing of rat corneal epithelial wound.

The invention claimed is:

1. A method for treating macular degeneration in a mammalian in need thereof, comprising: topically administering an eye drop formulation to the cornea of an eye of the mammalian, the eye drop formulation comprising as an active ingredient a therapeutically effective concentration of (2R,3R,4S)-6-amino-4-[N-(4-chlorophenyl)-N-(1H-imidazol-2-ylmethyl)amino]-3-hydroxy-2-methyl-2-dimethoxymethyl-3,4-dihydro-2H-1-benzopyran or a pharmaceutically acceptable salt, wherein the active ingredient is delivered to the retina without inhibiting normal regeneration of corneal epithelial cells, and wherein the therapeutically effective concentration is from 0.9 mg/mL to 10 mg/mL.

2. The method of claim 1, wherein the eye drop formulation is a solution or a suspension.

3. The method of claim 1, wherein the eye drop formulation is applied to the cornea of an eye from 1 to 6 times per day.

4. The method of claim 1, wherein the eye drop formulation is applied to the cornea of an eye from 2 to 4 times per day.

* * * * *

UNITED STATES PATENT AND TRADEMARK OFFICE
CERTIFICATE OF CORRECTION

PATENT NO.         : 10,485,786 B2                                   Page 1 of 1
APPLICATION NO.    : 15/941856
DATED              : November 26, 2019
INVENTOR(S)        : Kyu-Yang Yi et al.

It is certified that error appears in the above-identified patent and that said Letters Patent is hereby corrected as shown below:

On the Title Page (63):
Please delete "Mar. 29, 2011"
And replace with -- Mar. 29, 2012 --

Signed and Sealed this
Eleventh Day of February, 2020

Andrei Iancu
*Director of the United States Patent and Trademark Office*